United States Patent
Derynck et al.

(10) Patent No.: US 10,004,748 B2
(45) Date of Patent: Jun. 26, 2018

(54) METHODS OF TREATING PR-POSITIVE, LUMINAL A BREAST CANCER WITH PI3K INHIBITOR, PICTILISIB

(71) Applicant: Genentech, Inc., South San Francisco, CA (US)

(72) Inventors: Mika K. Derynck, San Mateo, CA (US); Lori Friedman, San Carlos, CA (US); Steven Brian Gendreau, Belmont, CA (US); Sandra Milan, Orinda, CA (US)

(73) Assignee: Genentech, Inc., South San Francisco, CA (US)

( * ) Notice: Subject to any disclaimer, the term of this patent is extended or adjusted under 35 U.S.C. 154(b) by 228 days.

(21) Appl. No.: 14/717,069

(22) Filed: May 20, 2015

(65) Prior Publication Data

US 2015/0335650 A1    Nov. 26, 2015

Related U.S. Application Data

(60) Provisional application No. 62/001,205, filed on May 21, 2014.

(51) Int. Cl.
| | | |
|---|---|---|
| *A61K 31/5377* | (2006.01) | |
| *A61K 45/06* | (2006.01) | |
| *C12Q 1/68* | (2018.01) | |
| *A61K 31/4196* | (2006.01) | |
| *A61K 31/565* | (2006.01) | |
| *C12Q 1/6886* | (2018.01) | |
| *G01N 33/574* | (2006.01) | |
| *G01N 33/50* | (2006.01) | |
| *A61K 31/381* | (2006.01) | |
| *A61K 31/495* | (2006.01) | |

(52) U.S. Cl.
CPC ........ *A61K 31/5377* (2013.01); *A61K 31/381* (2013.01); *A61K 31/4196* (2013.01); *A61K 31/495* (2013.01); *A61K 31/565* (2013.01); *A61K 45/06* (2013.01); *C12Q 1/6886* (2013.01); *G01N 33/5011* (2013.01); *G01N 33/57415* (2013.01); *C12Q 2600/118* (2013.01); *C12Q 2600/156* (2013.01); *C12Q 2600/158* (2013.01); *G01N 2333/916* (2013.01); *G01N 2333/91215* (2013.01)

(58) Field of Classification Search
CPC .............. A61K 31/5377; A61K 31/381; A61K 31/4196; A61K 31/495; A61K 31/565; A61K 45/06; C12Q 1/6886
See application file for complete search history.

(56) References Cited

U.S. PATENT DOCUMENTS

| | | | |
|---|---|---|---|
| 7,750,002 B2 | 7/2010 | Shuttleworth et al. | |
| 7,781,433 B2 | 8/2010 | Chuckowree et al. | |
| 8,247,397 B2 | 8/2012 | Belvin et al. | |
| 8,324,206 B2 | 12/2012 | Chuckowree et al. | |
| 8,536,161 B2 | 9/2013 | Ebens et al. | |
| 8,604,014 B2 | 10/2013 | Belvin et al. | |
| 2013/0096116 A1 | 4/2013 | Dalziel et al. | |

FOREIGN PATENT DOCUMENTS

| | | |
|---|---|---|
| WO | 2013049581 A1 | 4/2013 |
| WO | 2013/075059 A1 | 5/2013 |

OTHER PUBLICATIONS

ClinicalTrials identifier NCT01437566 (updated, Apr. 18, 2013).*
Chou and Talalay, "Quantitative analysis of dose-effect relationships: the combined effects of multiple drugs or enzyme inhibitors" Adv Enzyme Regul. 22:27-55 ( 1984).
Edgar et al., "Amphiregulin and PTEN evoke a multimodal mechanism of acquired resistance to PI3K inhibition" Genes Cancer 5( Suppl 3-4):113-26 ( 2014).
Edgar et al., "Isoform-Specific Phosphoinositide 3-Kinase Inhibitors Exert Distinct Effects in Solid Tumors" Cancer Res 70(3):1164-1172 (Feb. 1, 2010).
Flemming et al., "Fulvestrant for systemic therapy of locally advanced or metastatic breast cancer in postmenopausal women: a systematic review" Breast Cancer Res Treat. 115(2):255-68 ( 2009).
Floris et al., "A potent combination of the novel PI3K Inhibitor, GDC-0941, with imatinib in gastrointestinal tumor xenografts: long-lasting responses after treatment withdrawal. Epub Dec. 11, 2012" Clin Cancer Res. 19(3):620-30 ( 2013).
Folkes et al., "The identification of 2-(1H-indazol-4-yl)-6-(4-methanesulfonyl-piperazin-1-ylmethyl)-4-morpholin-4-yl-thieno[3,2-d]pyrimidine (GDC-0941) as a potent, selective, orally bioavailable inhibitor of class I PI3 kinase for the treatment of cancer" J Med Chem 51(18):5522-5532 ( 2008).
Friedman et al., "Selective PI3K and dual PI3K/mTOR inhibitors enhance the efficacy of endocrine therapies in breast cancer models" Cancer Research—AACR San Antonio Breast Cancer Symposium (Abstract), 72(24 Suppl 3) (Dec. 4-8, 2012).
Hoeflich et al., "In vivo Antitumor Activity of MEK and Phosphatidylinositol 3-Kinase Inhibitors in Basal-Like Breast Cancer Models" Clin Cancer Res 15(14):4649-4664 (Jul. 15, 2009).

(Continued)

*Primary Examiner* — Samantha L Shterengarts
(74) *Attorney, Agent, or Firm* — Zong-Qiang Bill Tian

(57) ABSTRACT

Methods and compositions are provided for treating breast cancer in patients with a PI3K inhibitor, GDC-0941 in combination with an endocrine therapy agent.

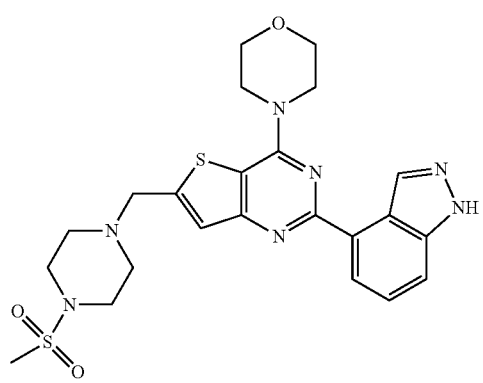

GDC-0941

27 Claims, 12 Drawing Sheets

(56) References Cited

OTHER PUBLICATIONS

Hoeflich et al., "Intermittent administration of MEK inhibitor GDC-0973 plus PI3K inhibitor GDC-0941 triggers robust apoptosis and tumor growth inhibition" Cancer Res 72(1):210-219 (Jan. 1, 2012).
ISR for PCT/EP2015/061051, WO 2015/177184.
Janku et al., "PIK3CA Mutations in Patients with Advanced Cancers Treated with PI3K/AKT/mTOR Axis Inhibitors" Mol Cancer Ther 10(3):558-65 ( 2011).
Junttila et al., "Ligand-independent HER2/HER3/PI3K complex is disrupted by trastuzumab and is effectively inhibited by the P13K inhibitor GDC-0941" Cancer Cell 15(5):429-40 ( 2009).
Miller et al., "Phosphatidylinositol 3-Kinase and Antiestrogen Resistance in Breast Cancer" J Clin Oncol 29:4452-4461 ( 2011).
Munugalavadla et al., "The P13K inhibitor GDC-0941 combines with existing clinical regimens for superior activity in multiple myeloma" Oncogene 33:316-325 ( 2014).
O'Brien et al., "Predictive Biomarkers of Sensitivity to the Phosphatidylinositol 3 Kinase Inhibitor GDC-0941 in Breast Cancer Preclinical Models" Clin Cancer Res 16(14):3670-3683 (Jul. 15, 2010).
Raynaud et al. et al., "Biological properties of potent inhibitors of class I phophatidylinositide 3-kinases: from PI-103 through PI-540, PI-620 to the oral agent GDC-0941" Mol Cancer Ther 8(7):1725-1738 (Jul. 2009).
Rouzier et al., "Breast cancer molecular subtypes respond differently to preoperative chrmotherapy" Clin Cancer Res. 11(16):5678-85 ( 2005).
Sampath et al., "Multimodal microvascular imaging reveals that selective inhibition of class I PI3K is sufficient to induce an antivascular response" Neoplasia 15(7):694-711 ( 2013).
Samuels et al., "High frequency of mutations of the PIK3CA gene in human cancers" Science 304:554 (Apr. 23, 2004).
Sarker et al., "First-in-human phase I study of pictilisib (GDC-0941), a potent pan-class I phosphatidylinositol-3-kinase (PI3K) inhibitor, in patients with advanced solid tumors" Clin Cancer Res. 21(1):77-8 ( 2015).
She et al., "Breast Tumor Cells with PI3K Mutation or HER2 Amplification Are Selectively Addicted to Akt Signaling" PLoS ONE 3(8):1-10 ( 2008).
Sos et al. et al., "Identifying genotype-dependent efficacy of single and combined PI3K- and MAPK-pathway inhibition in cancer" P Natl Acad Sci USA 106(43):18351-18356 (Oct. 27, 2009).
Spoerke et al., "Phosphoinositide 3-Kinase (PI3K) Pathway Alterations Are Associated with Histologic Subtypes and Are Predictive of Sensitivity to PI3K Inhibitors in Lung Cancer Preclinical Models" Clin Cancer Res 18:6771-83 ( 2012).
Sutherlin et al., "Discovery of (Thienopyrimidin-2-yl)aminopyrimidines as Potent, Selective, and Orally Available Pan-PI3-Kinase and Dual Pan-PI3-Kinase/mTOR Inhibitors for the Treatment of Cancer" J Med Chem 53(3):1086-1097 ( 2010).
Sutherlin et al., "Discovery of a potent, selective, and orally available class I phosphatidylinositol 3-kinase (PI3K)/mammalian target of rapamycin (mTOR) kinase inhibitor (GDC-0980) for the treatment of cancer" J Med Chem. 54(21):7579-87 ( 2011).
Vadas, "Structural Basis for Activation and Inhibition of Class I Phosphoinositide 3-Kinases" Science Signaling 4(195):1-12 (2011).
Wallin et al., "GDC-0941, a Novel Class I Selective PI3K Inhibitor, Enhances the Efficacy of Docetaxel in Human Breast Cancer Models by Increasing Cell Death In Vitro and In Vivo" Clin Cancer Res 18:3901-11 ( 2012).
Wallin et al., "GDC-0980 is a novel class I PI3K/mTOR kinase inhibitor with robust activity in cancer models driven by the PI3K pathway" Mol Cancer Ther. 10(12):2426-36 ( 2011).
Wallin et al., "Nuclear Phospho-Akt Increase Predicts Synergy of PI3K Inhibition and Doxorubicin in Breast and Ovarian Cancer" Sci Transl Med 2:48ra66 ( 2010).
Weigelt et al., "PIK3CA mutation, but not PTEN loss of function, determines the sensitivity of breast cancer cells to mTOR inhibitory drugs" Oncogene 30:3222-33 ( 2011).
Yao et al. et al., "Suppression of HER2/HER3-Mediated Growth of Breast Cancer Cells with Combinations of GDC-0941 PI3K Inhibitor, Trastuzumab, and Pertuzumab" Clin Cancer Res 15(12):4147-4156 (Jun. 15, 2009).
Krop et al., "Pictilisib for oestrogen recepto-positive, aromatase inhibitor-resistant, advanced or metastatic breast cancer (FERGI): a randomised, doubl-blind, placebo-controlled, phase 2 trial" The Lancet 14:811-821 (Jun. 2016).

* cited by examiner

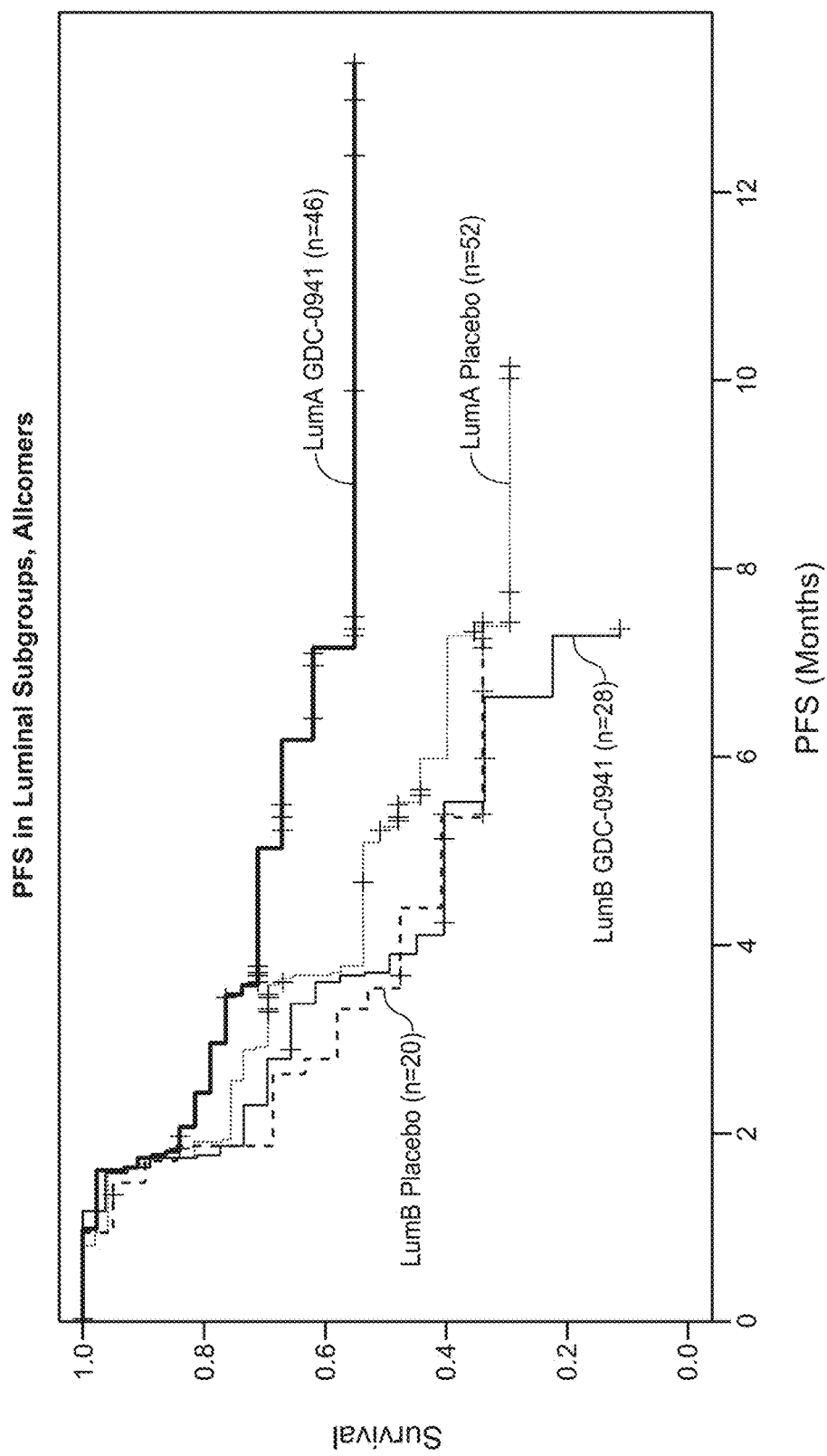

METHODS OF TREATING PR-POSITIVE, LUMINAL A BREAST CANCER WITH PI3K INHIBITOR, PICTILISIB

CROSS REFERENCE TO RELATED APPLICATIONS

This non-provisional application filed under 37 CFR § 1.53(b), claims the benefit under 35 USC § 119(e) of U.S. Provisional Application Ser. No. 62/001,205 filed on 21 May 2014, which is incorporated by reference in entirety.

FIELD OF THE INVENTION

The invention relates generally to treatment of hyperproliferative disorders such as cancer with compounds that inhibit PI3 kinase activity. The invention also relates to methods of using the compounds for in vitro, in situ, and in vivo diagnosis or treatment of mammalian cells, or associated pathological conditions.

BACKGROUND OF THE INVENTION

Phosphatidylinositol is one of a number of phospholipids found in cell membranes, and which participate in intracellular signal transduction. Cell signaling via 3'-phosphorylated phosphoinositides has been implicated in a variety of cellular processes, e.g., malignant transformation, growth factor signaling, inflammation, and immunity (Rameh et al (1999) J. Biol Chem. 274:8347-8350). The enzyme responsible for generating these phosphorylated signaling products, phosphatidylinositol 3-kinase (also referred to as PI 3-kinase or PI3K), was originally identified as an activity associated with viral oncoproteins and growth factor receptor tyrosine kinases that phosphorylate phosphatidylinositol (PI) and its phosphorylated derivatives at the 3'-hydroxyl of the inositol ring (Panayotou et al (1992) Trends Cell Biol 2:358-60). Phosphoinositide 3-kinases (PI3K) are lipid kinases that phosphorylate lipids at the 3-hydroxyl residue of an inositol ring (Whitman et al (1988) Nature, 332:664). The 3-phosphorylated phospholipids (PIP3s) generated by PI3-kinases act as second messengers recruiting kinases with lipid binding domains (including plekstrin homology (PH) regions), such as Akt and PDK1, phosphoinositide-dependent kinase-1 (Vivanco et al (2002) Nature Rev. Cancer 2:489; Phillips et al (1998) Cancer 83:41).

The PI3 kinase family comprises at least 15 different enzymes sub-classified by structural homology and are divided into 3 classes based on sequence homology and the product formed by enzyme catalysis. The class I PI3 kinases are composed of 2 subunits: a 110 kd catalytic subunit and an 85 kd regulatory subunit. The regulatory subunits contain SH2 domains and bind to tyrosine residues phosphorylated by growth factor receptors with a tyrosine kinase activity or oncogene products, thereby inducing the PI3K activity of the p110 catalytic subunit which phosphorylates its lipid substrate. Class I PI3 kinases are involved in important signal transduction events downstream of cytokines, integrins, growth factors and immunoreceptors, which suggests that control of this pathway may lead to important therapeutic effects such as modulating cell proliferation and carcinogenesis. Class I PI3Ks can phosphorylate phosphatidylinositol (PI), phosphatidylinositol-4-phosphate, and phosphatidylinositol-4,5-biphosphate (PIP2) to produce phosphatidylinositol-3-phosphate (PIP), phosphatidylinositol-3,4-biphosphate, and phosphatidylinositol-3,4,5-triphosphate, respectively. Class II PI3Ks phosphorylate PI and phosphatidylinositol-4-phosphate. Class III PI3Ks can only phosphorylate PI. A key PI3-kinase isoform in cancer is the Class I PI3-kinase, p110α as indicated by recurrent oncogenic mutations in p110α (Samuels et al (2004) Science 304:554; U.S. Pat. Nos. 5,824,492; 5,846,824; 6,274,327). Other isoforms may be important in cancer and are also implicated in cardiovascular and immune-inflammatory disease (Workman P (2004) Biochem Soc Trans 32:393-396; Patel et al (2004) Proc. Am. Assoc. of Cancer Res. (Abstract LB-247) 95th Annual Meeting, March 27-31, Orlando, Fla., USA; Ahmadi K and Waterfield M D (2004) "Phosphoinositide 3-Kinase: Function and Mechanisms" Encyclopedia of Biological Chemistry (Lennarz W J, Lane M D eds) Elsevier/Academic Press), Oncogenic mutations of p110 alpha have been found at a significant frequency in colon, breast, brain, liver, ovarian, gastric, lung, and head and neck solid tumors. About 35-40% of hormone receptor positive (HR+) breast cancer tumors harbor a PIK3CA mutation. PTEN abnormalities are found in glioblastoma, melanoma, prostate, endometrial, ovarian, breast, lung, head and neck, hepatocellular, and thyroid cancers.

Upregulation of the phosphoinositide-3 kinase (PI3K)/Akt signaling pathway is a common feature in most cancers (Yuan and Cantley (2008) Oncogene 27:5497-510). Genetic deviations in the pathway have been detected in many human cancers (Osaka et al (2004) Apoptosis 9:667-76) and act primarily to stimulate cell proliferation, migration and survival. Activation of the pathway occurs following activating point mutations or amplifications of the PIK3CA gene encoding the p110a PI3K isoforms (Hennessy et al (2005) Nat. Rev. Drug Discov. 4:988-1004). Genetic deletion or loss of function mutations within the tumor suppressor PTEN, a phosphatase with opposing function to PI3K, also increases PI3K pathway signaling (Zhang and Yu (2010) Clin. Cancer Res. 16:4325-30. These aberrations lead to increased downstream signaling through kinases such as Akt and mTOR and increased activity of the PI3K pathway has been proposed as a hallmark of resistance to cancer treatment (Opel et al (2007) Cancer Res. 67:735-45; Razis et al (2011) Breast Cancer Res. Treat. 128:447-56).

PI3 kinase is a heterodimer consisting of p85 and p110 subunits (Otsu et al (1991) Cell 65:91-104; Hiles et al (1992) Cell 70:419-29). Four distinct Class I PI3Ks have been identified, designated PI3K α (alpha), β (beta), δ (delta), and ω (gamma), each consisting of a distinct 110 kDa catalytic subunit and a regulatory subunit. Three of the catalytic subunits, i.e., p110 alpha, p110 beta and p110 delta, each interact with the same regulatory subunit, p85; whereas p110 gamma interacts with a distinct regulatory subunit, p101. The patterns of expression of each of these PI3Ks in human cells and tissues are distinct. In each of the PI3K alpha, beta, and delta subtypes, the p85 subunit acts to localize PI3 kinase to the plasma membrane by the interaction of its SH2 domain with phosphorylated tyrosine residues (present in an appropriate sequence context) in target proteins (Rameh et al (1995) Cell, 83:821-30; Volinia et al (1992) Oncogene, 7:789-93).

Measuring expression levels of biomarkers (e.g., secreted proteins in plasma) can be an effective means to identify patients and patient populations that will respond to specific therapies including, e.g., treatment with therapeutic agents. There is a need for more effective means for determining which patients with hyperproliferative disorders such as cancer will respond to which treatment with therapeutic agents, and for incorporating such determinations into more effective treatment regimens for patients, whether the therapeutic agents are used as single agents or combined with other agents.

The PI3 kinase/Akt/PTEN pathway is an attractive target for cancer drug development since such agents would be expected to inhibit cellular proliferation, to repress signals from stromal cells that provide for survival and chemoresistance of cancer cells, to reverse the repression of apoptosis and surmount intrinsic resistance of cancer cells to cytotoxic agents. PI3 kinase inhibitors have been reported (Yaguchi et al (2006) Jour. of the Nat. Cancer Inst. 98(8):545-556; U.S. Pat. Nos. 7,173,029; 7,037,915; 6,608,056; 6,608,053; 6,838,457; 6,770,641; 6,653,320; 6,403,588; 7,750,002; WO 2006/046035; U.S. Pat. No. 7,872,003; WO 2007/042806; WO 2007/042810; WO 2004/017950; US 2004/092561; WO 2004/007491; WO 2004/006916; WO 2003/037886; US 2003/149074; WO 2003/035618; WO 2003/034997; US 2003/158212; EP 1417976; US 2004/053946; JP 2001247477; JP 08175990; JP 08176070).

Certain thienopyrimidine compounds have p110 alpha binding, PI3 kinase inhibitory activity, and inhibit the growth of cancer cells (Wallin et al (2011) Mol. Can. Ther. 10(12):2426-2436; Sutherlin et al (2011) Jour. Med. Chem. 54:7579-7587; US 2008/0207611; U.S. Pat. Nos. 7,846,929; 7,781,433; US 2008/0076758; U.S. Pat. No. 7,888,352; US 2008/0269210. GDC-0941 (CAS Reg. No. 957054-30-7, Genentech Inc.), is a selective, orally bioavailable inhibitor of PI3K with promising pharmacokinetic and pharmaceutical properties (Folkes et al (2008) Jour. of Med. Chem. 51(18):5522-5532; U.S. Pat. No. 7,781,433; Belvin et al, American Association for Cancer Research Annual Meeting 2008, 99th:April 15, Abstract 4004; Folkes et al, American Association for Cancer Research Annual Meeting 2008, 99th:April 14, Abstract LB-146; Friedman et al (2008), American Association for Cancer Research Annual Meeting 2008, 99th:April 14, Abstract LB-110) and shows synergistic activity in vitro and in vivo in combination with certain chemotherapeutic agents against solid tumor cell lines (US 2009/0098135).

New targeted treatments that increase treatment responsiveness, delay disease progression, improve tolerability, and potentially eradicate chemotherapy-resistant malignant cells would represent a significant advance in the care of women with breast cancer. The principal strategy for the treatment of patients with hormone receptor positive (HR+) metastatic breast cancer (MBC) has been to block the action of estrogen at the level of the receptor or to reduce estrogen production. Breast cancer is known to be a heterogeneous disease. Different subtypes exist which can be defined based on: (i) the molecular profile of the breast cancer tumor; (ii) genetic array testing; or (iii) approaches using immunohistochemical analyses. Most breast cancers are luminal tumors. Luminal tumor cells look the most like the cells of breast cancers that start in the inner (luminal) cells lining the mammary ducts. Molecular subtypes of breast cancer may be useful in planning treatment and developing new therapies, including: Luminal A, Luminal B, Triple negative/basal-like, and HER2 type. The Luminal A subtype represents about 40% of breast cancer and tends to be ER+ (estrogen receptor-positive) and/or PR+ (progesterone receptor-positive), HER2− (HER2/neu receptor-negative), low Ki67. ER/PR/HER2 are clinically validated predictive and prognostic biomarkers. Proliferation marker Ki-67 is an exemplary prognostic parameter in breast cancer patients.

Aromatase inhibitors (AIs), such as anastrozole, letrozole, and exemestane, block peripheral estrogen synthesis by inhibiting aromatase, the enzyme responsible for the peripheral conversion of androgens to estrogen (Simpson and Dowsett (2002) Recent Prog Horm Res 57:317-38). Clinical trials have demonstrated the efficacy of both tamoxifen and AI therapy in the treatment of postmenopausal women with HR-positive MBC (Nabholtz et al. (2000) J Clin Oncol 18:3758-67; Mouridsen et al. (2001) J Clin Oncol 19:2596-606; Osborne et al. (2002) J Clin Oncol 20:3386-95; Howell et al. (2004) J Clin Oncol 22:1605-13; Paridaens et al. (2004) Proceedings Am Soc Clin Oncol 22:14S). In addition, fulvestrant, an estrogen receptor (ER) antagonist that down-regulates ER protein levels, has been approved by the U.S. Food and Drug Administration (FDA) for HR-positive MBC and European Medicines Agency (EMA) for the treatment of ER-positive MBC in postmenopausal women with disease progression following previous anti-estrogen therapy (Howell et al. (2002) J Clin Oncol 20:3396-403; Osborne et al. (2002) J Clin Oncol 20:3386-95; Di Leo et al. (2010) J Clin Oncol 28:4594-600). Although existing treatments can provide some delay in the progression of disease, the major limitation of endocrine therapy remains the nearly universal development of therapeutic resistance, which leads to eventual death in the overwhelming majority of patients. MBC remains the second highest cause of cancer death in women, emphasizing the continued unmet need in this disease.

Abnormal activation of the phosphoinositide 3-kinase (PI3K) pathway in cancer, either via genetic alterations in PI3K pathway constituents (PI3K-activating mutations or genetic amplification, loss of the antagonistic tumor suppressor PTEN) or via the transduction of aberrant receptor tyrosine kinase (RTK) signals, is a common finding in a variety of tumor types. This combined with the resistance to endocrine therapy suggests that inhibition of PI3K signaling could have broad application in the treatment of breast cancer.

Luminal A breast cancers have higher estrogen receptor (ER+) and/or progesterone receptor (PR+) expression than luminal B breast cancers. Luminal A breast cancer patients with these expression patterns respond well to endocrine, hormone therapy and have a generally favorable prognosis (Rouzier et al (2005) Clin. Cancer Res. 11:5678-5685).

The activity of endocrine therapies, including tamoxifen and AIs is the primary reason for the sustained improvement in survival for patients with early-stage HR-positive breast cancer. However, nearly half of the patients that present with metastatic HR-positive disease do not respond to front-line endocrine treatment and nearly all patients who do respond eventually develop resistance to endocrine therapy.

The mechanisms of resistance to hormonal therapies in HR-positive MBC patients are likely to be multifactorial. Nonclinical and clinical data suggest that decrease or loss of ER and/or PgR expression and upregulation of growth factor signaling are two of the prominent mechanisms leading to estrogen-independent tumor growth (Johnston 2009; Osborne and Schiff 2011). The loss of ER expression over time has been observed in up to 20% of the patients treated with endocrine therapy (Gutierrez et al. 2005), which might account for acquired anti-estrogen resistance and subsequent disease progression. ER expression has been shown to be regulated through multiple growth factor-signaling pathways. In particular, activation of the EGFR/HER2 and mitogen-activated protein kinase (MAPK) pathway leads to suppression of ER expression resulting in resistance to tamoxifen (McClelland et al. 2001; Knowlden et al. 2003; Hutcheson et al. 2003). In addition to modulating ER levels, growth factor-signaling pathways can directly enhance the transcriptional activity of ER via direct phosphorylation of the receptor at serine 118 and serine 167 (Chen et al. 2002; Campbell et al. 2001). "Non-genomic" activities of ER have been postulated to stimulate a number of intracellular signaling pathways including the MAPK and PI3K pathways in the cytosol (Bjornstrom and Sjöberg 2005; Acconcia et al. 2005). These non-genomic activities have been proposed as an important feature in endocrine response and resistance in breast cancer (Schiff et al. 2003).

Multiple lines of nonclinical and clinical data support a key role for the PI3K pathway in the generation of resistance to hormonal therapies. Activation of the PI3K pathway (via PIK3CA mutations, loss of PTEN expression, or HER2 overexpression) has been demonstrated to promote resistance to anti-estrogen therapy and hormonal independence in ER-positive breast cancer models (Shou et al. (2004) J Natl Cancer Inst 96:926-3; Miller et al. (2009) Cancer Res 2009; 69:4192-201, Miller et al. (2010) J Clin Invest 120: 2406-13). Proteomic and transcriptional profiling of human HR-positive tumors suggest that increased PI3K signaling is associated with lower ER levels, which has been correlated with resistance to endocrine therapy (Creighton et al. 2010; Miller et al. (2010) J Clin Invest 120:2406-13). Retrospective analyses of tumor samples from HR-positive patients treated with tamoxifen lend support to the nonclinical observations linking the PI3K pathway to resistance to anti-estrogen therapy; patients with an activated PI3K pathway have been found to have decreased overall survival (OS) (Kirkegaard et al. (2005) J Pathol 207:139-46) and shorter relapse-free survival (Shoman et al. (2005) Mod Pathol 18:250-9) Inhibition of the PI3K/mTOR pathway in nonclinical models has been shown to upregulate ER/PgR expression (Creighton et al. 2010) and enhance the antitumor effect of letrozole (Boulay et al. 2005).

In the clinical setting, data from two Phase II studies suggest that the combined inhibition of the PI3K/mTOR and estrogen-signaling pathway may provide superior benefit when compared to single-agent endocrine therapies. Administration of a rapalog, everolimus, increased the efficacy of letrozole in the neoadjuvant setting in patients with ER-positive breast cancer as measured by a decrease in Ki67 expression (Baselga et al. 2009). The addition of everolimus to tamoxifen in a Phase II study with ER-positive patients who received prior treatment with an AI significantly improved the clinical benefit rate (CBR), time to progression and overall survival compared to single-agent tamoxifen (Bachelot et al. 2012). Finally, data from the Phase III BOLERO-2 study demonstrated that the addition of everolimus to exemestane more than doubled PFS compared with single-agent exemestane in ER-positive, HER2-negative MBC patients whose disease was refractory to prior treatment with letrozole or anastrozole (Baselga et al. 2012). Therefore, the combined inhibition of the ER and PI3K-pathways may prove to be an effective therapy in patients with MBC who experience recurrent or progressive disease (PD) while receiving treatment with an AI.

GDC-0941 (pictrelisib, pictilisib, Genentech Inc., Roche, RG-7321, CAS Reg. No. 957054-30-7), named as 4-(2-(1H-indazol-4-yl)-6-((4-(methylsulfonyl)piperazin-1-yl)methyl)thieno[3,2-d]pyrimidin-4-yl)morpholine, has potent PI3K activity (WO 2011/036280; U.S. Pat. Nos. 8,242,104; 8,343, 955) and is being studied in patients with locally advanced or metastatic solid tumors. GDC-0941 is a weak inhibitor of Class II, III, and IV PI3K family members (including DNA-dependent protein kinase and mammalian target of rapamycin [mTOR], with >250-fold selectivity for p110α). GDC-0941 potently inhibits in vitro growth of a broad array of breast cancer cell lines by inducing G1 arrest and apoptosis (Friedman et al. (2009) AACR-NCI-EORTC Molecular Targets and Cancer Therapeutics, 15-19 Nov. 2009, Boston, Mass. Abstract C201; O'Brien et al. (2010) Clin Cancer Res 16:3670-83). GDC-0941 has exceeded its minimum effective target dose (an exposure associated with 90% tumor grown inhibition in preclinical models) in Phase I testing, and has demonstrated pharmacodynamic and anti-tumor activity at tolerable doses (Baird et al. (2010) J Clin Oncol 2010 ASCO Annual Meeting Proceedings (Post-Meeting Edition) 2010; 28(15 Suppl):2613; Dolly et al. (2010) J Clin Oncol 2010 ASCO Annual Meeting Proceedings (Post-Meeting Edition) 28(15 Suppl):3079; Von Hoff et al. (2010) J Clin Oncol 2010 ASCO Annual Meeting Proceedings 2010; 28(15 Suppl):2541).

SUMMARY OF THE INVENTION

GDC-0941 (pictrelisib, pictilisib, Genentech Inc., Roche, RG-7321) is a potent multitargeted class I (pan) inhibitor of PI3K isoforms. GDC-0941 is currently in phase II clinical trials for the treatment of advanced solid tumors. GDC-0941 is named as 4-(2-(1H-indazol-4-yl)-6-((4-(methylsulfonyl)piperazin-1-yl)methyl)thieno[3,2-d]pyrimidin-4-yl)morpholine (U.S. Pat. Nos. 7,781,433; 7,750,002; Folkes et al (2008) Jour. of Med. Chem. 51(18):5522-5532), and has the structure:

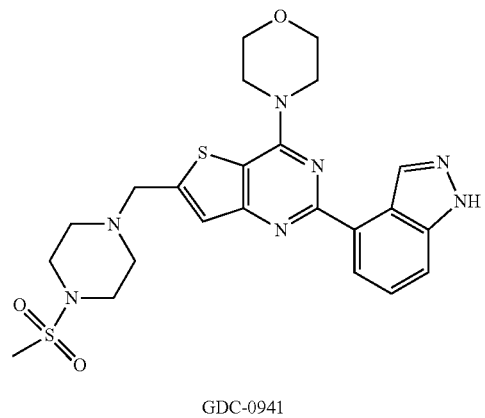 [SMILES: CS(=O)(=O)N1CCN(Cc2cc3nc(-c4cccc5[nH]ncc45)nc(N4CCOCC4)c3s2)CC1]

GDC-0941 including stereoisomers, geometric isomers, tautomers, and pharmaceutically acceptable salts thereof.

The invention provides methods of treating patients with PR+ or luminal A-type breast cancer by administration of a therapeutically effective amount of GDC-0941 and an endocrine therapy agent.

The invention also provides an article of manufacture for treating PR+, luminal A-type breast cancer comprising: GDC-0941; and instructions for use.

The invention also provides a method for determining compounds to be used in combination for the treatment of PR+, luminal A-type breast cancer comprising:

a) treating an in vitro tumor cell line with a PIK3CA mutation with a therapeutic combination of GDC-0941 and an endocrine therapy agent selected from fulvestrant, letrozole, tamoxifen, and exemestane, and b) measuring a synergistic or non-synergistic effect; whereby a synergistic therapeutic combination for the treatment of cancer is determined.

The invention also provides a method of selecting patients with PR+, luminal A-type breast cancer for treatment with GDC-0941 comprising:

(a) detecting a PIK3CA or PTEN mutation in a biological sample obtained from the patient; and (b) comparing PIK3CA or PTEN mutation status in a biological sample obtained from the patient prior to administration of GDC-0941 or the combination of GDC-0941 and an endocrine therapy agent to the patient, wherein a change or modulation of PIK3CA or PTEN mutation status in the sample obtained following administration of GDC-0941 or the combination of GDC-0941 and an endocrine therapy agent identifies a patient who will respond to treatment with GDC-0941.

The invention also provides a method of monitoring therapeutic efficacy in patients with PR+, luminal A-type breast cancer comprising:

(a) treating the patient with GDC-0941;

(b) measuring functional PI3K protein level in a biological sample obtained from the patient after administration of GDC-0941; and (c) altering the dosage of GDC-0941, the frequency of dosing GDC-0941, or the course of therapy administered to the patient.

The invention also provides a method of optimizing therapeutic efficacy of GDC-0941 or the combination of GDC-0941 and an endocrine therapy agent in the treatment of PR+, luminal A-type breast cancer, the method comprising:

(a) detecting a PIK3CA or PTEN mutation in a biological sample obtained from a patient following administration of at least one dose of GDC-0941 or the combination of GDC-0941 and an endocrine therapy agent selected from fulvestrant and letrozole; and (b) comparing the PIK3CA or PTEN status in a biological sample obtained from the patient prior to administration of GDC-0941 or the combination of GDC-0941 and an endocrine therapy agent to the patient, wherein a change or modulation of PIK3CA or PTEN in the sample obtained following administration of GDC-0941 or the combination of GDC-0941 and a therapeutic agent identifies a patient who has an increased likelihood of benefit from treatment with GDC-0941 or the combination of GDC-0941 and an endocrine therapy agent.

The invention also provides a method of identifying a biomarker for monitoring responsiveness to GDC-0941 or the combination of GDC-0941 and an endocrine therapy agent in the treatment of PR+, luminal A-type breast cancer, the method comprising:

(a) detecting the expression, modulation, or activity of a biomarker selected from a PIK3CA or PTEN mutation in a biological sample obtained from a patient who has received at least one dose of GDC-0941 or the combination of GDC-0941 and an endocrine therapy agent selected from fulvestrant, letrozole, tamoxifen, and exemestane; and (b) comparing the expression, modulation, or activity of the biomarker to the status of the biomarker in a reference sample wherein the reference sample is a biological sample obtained from the patient prior to administration of GDC-0941 or the combination of GDC-0941 and an endocrine therapy agent to the patient;

wherein the modulation of the biomarker changes by at least 2 fold lower or higher compared to the reference sample is identified as a biomarker useful for monitoring responsiveness to GDC-0941 or the combination of GDC-0941 and an endocrine therapy agent.

The invention also provides a use of GDC-0941 or a combination of GDC-0941 and a therapeutic agent in treating PR+, luminal A-type breast cancer in a patient comprising administering a therapeutically effective amount of GDC-0941 or the combination of GDC-0941 and an endocrine therapy agent selected from fulvestrant, letrozole, tamoxifen, and exemestane to the patient, wherein a biological sample obtained from the patient, prior to administration of GDC-0941 or the combination of GDC-0941 and a therapeutic agent to the patient, has been tested for PIK3CA or PTEN mutation status, and wherein PIK3CA or PTEN mutation status is indicative of therapeutic responsiveness by the patient to GDC-0941 or the combination of GDC-0941 and an endocrine therapy agent.

BRIEF DESCRIPTION OF THE DRAWINGS

FIG. 6 shows a Kaplan-Meier Plot of Progression-free Survival based on the intrinsic subtype analysis. Luminal B patients treated with GDC-0941+fulvestrant or placebo were compared with Luminal A patients treated with GDC-0941+fulvestrant or placebo.

DETAILED DESCRIPTION OF EXEMPLARY EMBODIMENTS

Figure 1:
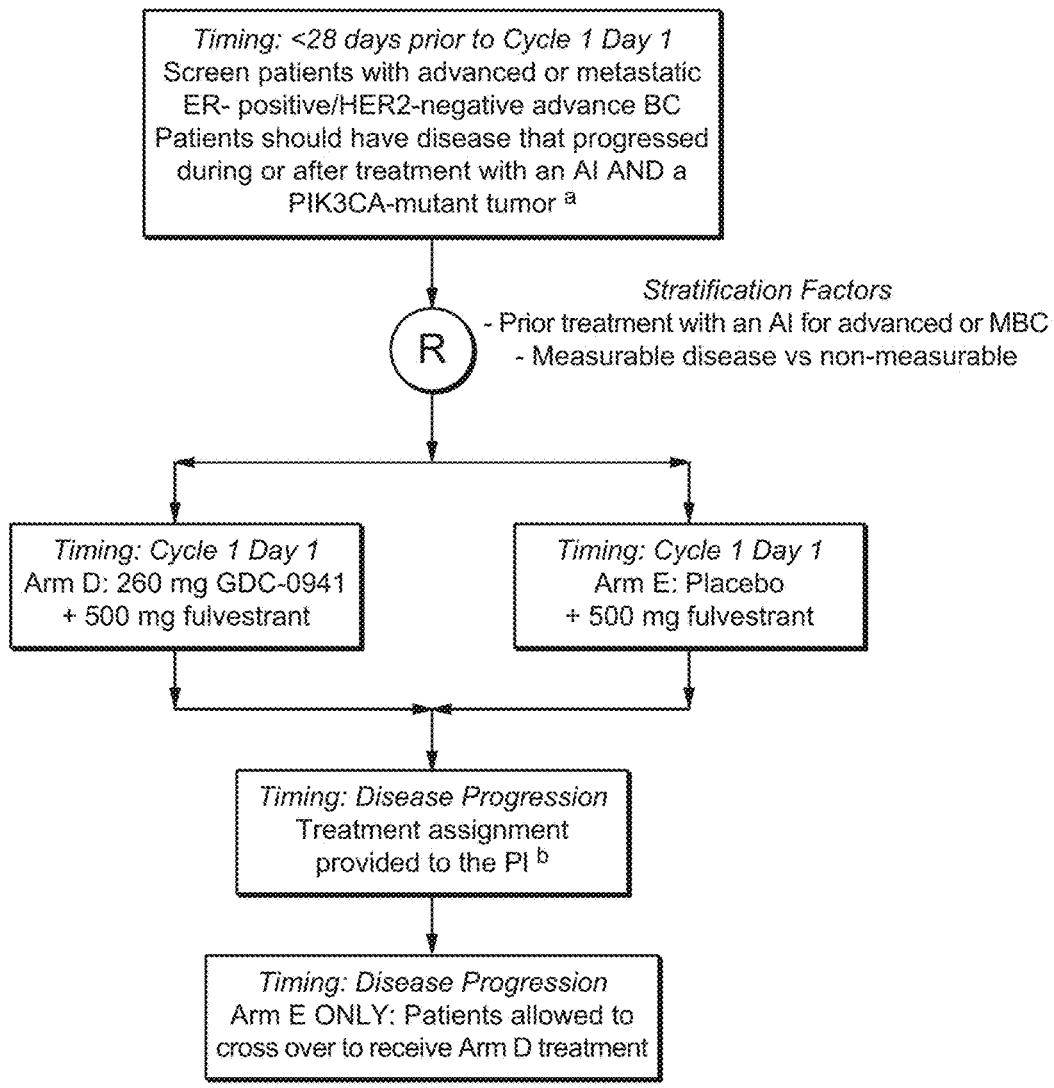
FIG. 1 shows the clinical study schema for treatment of ER-positive breast cancer patients with GDC-0941 in combination with fulvestrant.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

Definitions

The words "comprise," "comprising," "include," "including," and "includes" when used in this specification and claims are intended to specify the presence of stated features, integers, components, or steps, but they do not preclude the presence or addition of one or more other features, integers, components, steps, or groups thereof.

The terms "treat" and "treatment" refer to both therapeutic treatment and prophylactic or preventative measures, wherein the object is to prevent or slow down (lessen) an undesired physiological change or disorder, such as the growth, development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The term "detection" includes any means of detecting, including direct and indirect detection.

The term "diagnosis" is used herein to refer to the identification or classification of a molecular or pathological state, disease or condition. For example, "diagnosis" may refer to identification of a particular type of cancer, e.g., a lung cancer. "Diagnosis" may also refer to the classification of a particular type of cancer, e.g., by histology (e.g., a non-small cell lung carcinoma), by molecular features (e.g., a lung cancer characterized by nucleotide and/or amino acid variation(s) in a particular gene or protein), or both.

The term "prognosis" is used herein to refer to the prediction of the likelihood of cancer-attributable death or progression, including, for example, recurrence, metastatic spread, and drug resistance, of a neoplastic disease, such as cancer.

The term "prediction" (and variations such as predicting) is used herein to refer to the likelihood that a patient will respond either favorably or unfavorably to a drug or set of drugs. In one embodiment, the prediction relates to the extent of those responses. In another embodiment, the prediction relates to whether and/or the probability that a patient will survive following treatment, for example treatment with a particular therapeutic agent and/or surgical removal of the primary tumor, and/or chemotherapy for a certain period of time without cancer recurrence. The predictive methods of the invention can be used clinically to make treatment decisions by choosing the most appropriate treatment modalities for any particular patient. The predictive methods of the present invention are valuable tools in predicting if a patient is likely to respond favorably to a treatment regimen, such as a given therapeutic regimen, including for example, administration of a given therapeutic agent or combination, surgical intervention, chemotherapy, etc., or whether long-term survival of the patient, following a therapeutic regimen is likely.

The term "increased resistance" to a particular therapeutic agent or treatment option, when used in accordance with the invention, means decreased response to a standard dose of the drug or to a standard treatment protocol.

The term "decreased sensitivity" to a particular therapeutic agent or treatment option, when used in accordance with the invention, means decreased response to a standard dose of the agent or to a standard treatment protocol, where decreased response can be compensated for (at least partially) by increasing the dose of agent, or the intensity 5 of treatment.

"Patient response" can be assessed using any endpoint indicating a benefit to the patient, including, without limitation, (1) inhibition, to some extent, of tumor growth, including slowing down or complete growth arrest; (2) reduction in the number of tumor cells; (3) reduction in tumor size; (4) inhibition (e.g., reduction, slowing down or complete stopping) of tumor cell infiltration into adjacent peripheral organs and/or tissues; (5) inhibition (e.g., reduction, slowing down or complete stopping) of metastasis; (6) enhancement of anti-tumor immune response, which may, but does not have to, result in the regression or rejection of the tumor; (7) relief, to some extent, of one or more symptoms associated with the tumor; (8) increase in the length of survival following treatment; and/or (9) decreased mortality at a given point of time following treatment.

A "biomarker" is a characteristic that is objectively measured and evaluated as an indicator of normal biological processes, pathogenic processes, or pharmacological responses to a therapeutic intervention. Biomarkers may be of several types: predictive, prognostic, or pharmacodynamics (PD). Predictive biomarkers predict which patients are likely to respond or benefit from a particular therapy. Prognostic biomarkers predict the likely course of the patient's disease and may guide treatment. Pharmacodynamic biomarkers confirm drug activity, and enables optimization of dose and administration schedule.

"Change" or "modulation" of the status of a biomarker, including a PIK3CA mutation or set of PIK3CA mutations, as it occurs in vitro or in vivo is detected by analysis of a biological sample using one or more methods commonly employed in establishing pharmacodynamics (PD), including: (1) sequencing the genomic DNA or reverse-transcribed PCR products of the biological sample, whereby one or more mutations are detected; (2) evaluating gene expression levels by quantitation of message level or assessment of copy number; and (3) analysis of proteins by immunohistochemistry, immunocytochemistry, ELISA, or mass spectrometry whereby degradation, stabilization, or post-translational modifications of the proteins such as phosphorylation or ubiquitination is detected.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer. Gastric cancer, as used herein, includes stomach cancer, which can develop in any part of the stomach and may spread throughout the stomach and to other organs; particularly the esophagus, lungs, lymph nodes, and the liver.

The term "hematopoietic malignancy" refers to a cancer or hyperproliferative disorder generated during hematopoiesis involving cells such as leukocytes, lymphocytes, natural killer cells, plasma cells, and myeloid cells such as neutrophils and monocytes. Hematopoietic malignancies include non-Hodgkin's lymphoma, diffuse large hematopoietic lymphoma, follicular lymphoma, mantle cell lymphoma, chronic lymphocytic leukemia, multiple myeloma, acute myelogenous leukemia, and myeloid cell leukemia. Lymphocytic leukemia (or "lymphoblastic") includes Acute lymphoblastic leukemia (ALL) and Chronic lymphocytic leukemia (CLL). Myelogenous leukemia (also "myeloid" or "nonlymphocytic") includes Acute myelogenous (or Myeloblastic) leukemia (AML) and Chronic myelogenous leukemia (CML).

An "endocrine therapy agent" is a biological (large molecule) or chemical (small molecule) compound useful in the treatment of cancer, regardless of mechanism of action. Examples of an endocrine therapy agent include, but are not limited to, fulvestrant, letrozole, tamoxifen, and exemestane.

Endocrine therapy agents may be (i) anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); or (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca).

A "therapeutic agent" is a biological (large molecule) or chemical (small molecule) compound useful in the treatment of cancer, regardless of mechanism of action.

The term "mammal" includes, but is not limited to, humans, mice, rats, guinea pigs, monkeys, dogs, cats, horses, cows, pigs and sheep.

The term "package insert" is used to refer to instructions customarily included in commercial packages of therapeutic products, that contain information about the indications, usage, dosage, administration, contraindications and/or warnings concerning the use of such therapeutic products.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

The desired pharmaceutically acceptable salt may be prepared by any suitable method available in the art. For example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. Acids which are generally considered suitable for the formation of pharmaceutically useful or acceptable salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1 19; P. Gould, International J. of Pharmaceutics (1986) 33 201 217; Anderson et al, The Practice of Medicinal Chemistry (1996), Academic Press, New York; Remington's Pharmaceutical Sciences, 18$^{th}$ ed., (1995) Mack Publishing Co., Easton Pa.; and in The Orange Book (Food & Drug Administration, Washington, D.C. on their website). These disclosures are incorporated herein by reference thereto.

The phrase "pharmaceutically acceptable" indicates that the substance or composition must be compatible chemically and/or toxicologically, with the other ingredients comprising a formulation, and/or the mammal being treated therewith.

The term "synergistic" as used herein refers to a therapeutic combination which is more effective than the additive effects of the two or more single agents. A determination of a synergistic interaction between a compound of GDC-0941 or a pharmaceutically acceptable salt thereof and one or more therapeutic agent may be based on the results obtained from the assays described herein. The results of these assays can be analyzed using the Chou and Talalay combination method and Dose-Effect Analysis with CalcuSyn software in order to obtain a Combination Index (Chou and Talalay, 1984, Adv. Enzyme Regul. 22:27-55). The combinations provided by this invention have been evaluated in several assay systems, and the data can be analyzed utilizing a standard program for quantifying synergism, additivism, and antagonism among anticancer agents described by Chou and Talalay, in "New Avenues in Developmental Cancer Chemotherapy," Academic Press, 1987, Chapter 2. Combination Index values less than 0.8 indicates synergy, values greater than 1.2 indicate antagonism and values between 0.8 and 1.2 indicate additive effects. The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes or in separate pills or tablets. In general, during alternation therapy, an effective dosage of each active ingredient is administered sequentially, i.e., serially, whereas in combination therapy, effective dosages of two or more active ingredients are administered together. Combination effects were evaluated using both the BLISS independence model and the highest single agent (HSA) model (Lehár et al. 2007, Molecular Systems Biology 3:80). BLISS scores quantify degree of potentiation from single agents and a BLISS score >0 suggests greater than simple additivity. An HSA score >0 suggests a combination effect greater than the maximum of the single agent responses at corresponding concentrations.

"ELISA" (Enzyme-linked immunosorbent assay) is a popular format of a "wet-lab" type analytic biochemistry assay that uses one sub-type of heterogeneous, solid-phase enzyme immunoassay (EIA) to detect the presence of a substance in a liquid sample or wet sample (Engvall E, Perlman P (1971). "Enzyme-linked immunosorbent assay (ELISA). Quantitative assay of immunoglobulin G". Immunochemistry 8 (9): 871-4; Van Weemen B K, Schuurs A H (1971). "Immunoassay using antigen-enzyme conjugates". FEBS Letters 15 (3): 232-236). ELISA can perform other forms of ligand binding assays instead of strictly "immuno" assays, though the name carried the original "immuno" because of the common use and history of development of this method. The technique essentially requires any ligating reagent that can be immobilized on the solid phase along with a detection reagent that will bind specifically and use an enzyme to generate a signal that can be properly quantified. In between the washes only the ligand and its specific binding counterparts remain specifically bound or "immunosorbed" by antigen-antibody interactions to the solid phase, while the nonspecific or unbound components are washed away. Unlike other spectrophotometric wet lab assay formats where the same reaction well (e.g. a cuvette) can be reused after washing, the ELISA plates have the reaction products immunosorbed on the solid phase which is part of the plate and thus are not easily reusable. Performing an ELISA involves at least one antibody with specificity for a particular antigen. The sample with an unknown amount of antigen is immobilized on a solid support (usually a polystyrene microtiter plate) either non-specifically (via adsorption to the surface) or specifically (via capture by another antibody specific to the same antigen, in a "sandwich" ELISA). After the antigen is immobilized, the detection antibody is added, forming a complex with the antigen. The detection antibody can be covalently linked to an enzyme, or can itself be detected by a secondary antibody that is linked to an enzyme through bioconjugation. Between each step, the plate is typically washed with a mild detergent solution to remove any proteins or antibodies that are not specifically bound. After the final wash step, the plate is developed by adding an enzymatic substrate to produce a visible signal, which indicates the quantity of antigen in the sample.

"Immunohistochemistry" (IHC) refers to the process of detecting antigens (e.g., proteins) in cells of a tissue section by exploiting the principle of antibodies binding specifically to antigens in biological tissues. Immunohistochemical staining is widely used in the diagnosis of abnormal cells such as those found in cancerous tumors. Specific molecular markers are characteristic of particular cellular events such as proliferation or cell death (apoptosis). IHC is also widely used to understand the distribution and localization of biomarkers and differentially expressed proteins in different parts of a biological tissue. Visualizing an antibody-antigen interaction can be accomplished in a number of ways. In the most common instance, an antibody is conjugated to an enzyme, such as peroxidase, that can catalyze a color-producing reaction (see immunoperoxidase staining) Alternatively, the antibody can also be tagged to a fluorophore, such as fluorescein or rhodamine (see immunofluorescence).

"Immunocytochemistry" (ICC) is a common laboratory technique that uses antibodies that target specific peptides or protein antigens in the cell via specific epitopes. These bound antibodies can then be detected using several different methods. ICC can evaluate whether or not cells in a particular sample express the antigen in question. In cases where an immunopositive signal is found, ICC also determines which sub-cellular compartments are expressing the antigen.

"Kaplan-Meier plot"-is an estimator for estimating the survival function from lifetime data (Kaplan, E. L.; Meier, P. (1958). "Nonparametric estimation from incomplete observations". J. Amer. Statist. Assn. 53 (282): 457-481). In medical research, it is often used to measure the fraction of patients living for a certain amount of time after treatment. The plot of the Kaplan-Meier estimate of the survival function is a series of horizontal steps of declining magnitude which, when a large enough sample is taken, approaches the true survival function for that population. The value of the survival function between successive distinct sampled observations ("clicks") is assumed to be constant.

Clinical Trial Drugs

GDC-0941 (pictrelisib, pictilisib, Genentech Inc., Roche, RG-7321, CAS Reg. No. 957054-30-7) is a potent multitargeted class I (pan) inhibitor of PI3K isoforms. GDC-0941 is currently in phase II clinical trials for the treatment of advanced solid tumors. GDC-0941 is named as 4-(2-(1H-indazol-4-yl)-6-((4-(methylsulfonyl)piperazin-1-yl)methyl) thieno[3,2-d]pyrimidin-4-yl)morpholine (U.S. Pat. Nos. 7,781,433; 7,750,002; Folkes et al (2008) Jour. of Med. Chem. 51(18):5522-5532), and has the structure:

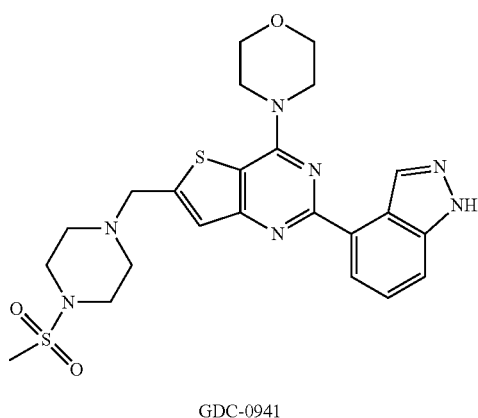 [SMILES: CS(=O)(=O)N1CCN(Cc2cc3nc(-c4cccc5[nH]ncc45)nc(N4CCOCC4)c3s2)CC1]

GDC-0941 including stereoisomers, geometric isomers, tautomers, and pharmaceutically acceptable salts thereof.

Figure 2:
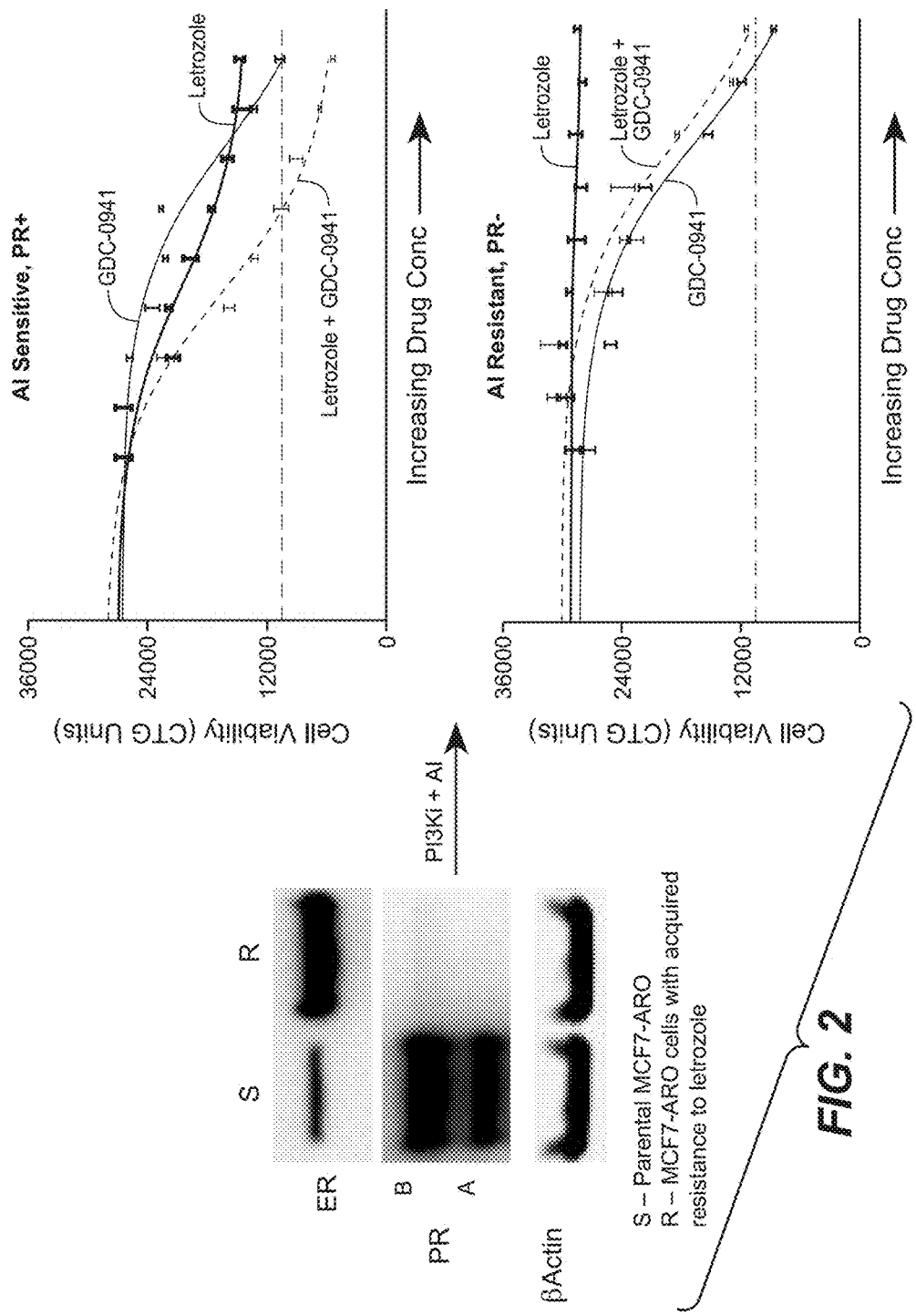
FIG. 2 shows plots of cell viability of PR+ aromatase inhibitor-sensitive (top) and PR-, aromatase inhibitor-resistant (bottom) cell lines MCF7-ARO (Wallin et al (2012) Clin Cancer Res; 18:3901-3911) treated with GDC-0941, letrozole, and the combination of GDC-0941 and letrozole.

The phosphoinositide 3-kinase (PI3K) signaling cascade, a key mediator of cellular survival, growth, and metabolism, is frequently altered in human cancer. Activating mutations in PIK3CA, the gene which encodes the α-catalytic subunit of PI3K, occur in approximately 30% of breast cancers. These mutations result in constitutive activity of the enzyme and are oncogenic. Expression of mutant PIK3CA H1047R in the luminal mammary epithelium evokes heterogeneous tumors that express luminal and basal markers and are positive for the estrogen receptor. The PIK3CA H1047R oncogene targets a multipotent progenitor cells and recapitulates features of human breast tumors with PIK3CA H1047R (Meyer et al (2011). Cancer Res; 71(13):4344-51). Hyperactivation of PI3K can occur as a result of somatic mutations in PIK3CA, the gene encoding the p110α subunit of PI3K. The HER2 oncogene is amplified in 25% of all breast cancers and some of these tumors also harbor PIK3CA mutations. PI3K can enhance transformation and confer resistance to HER2-directed therapies. PI3K mutations E545K and H1047R introduced in MCF10A human mammary epithelial cells that also overexpress HER2 conferred a gain of function to MCF10A/HER2 cells. Aromatase-expressing MCF7 cells convert androstenedione to estrogen in culture. FIG. 2 shows plots of cell viability of PR+ aromatase inhibitor-sensitive (top) and PR−, aromatase inhibitor-resistant (bottom) cell lines MCF7-ARO (Wallin et al (2012) Clin Cancer Res; 18:3901-3911) treated with GDC-0941, letrozole, and the combination of GDC-0941 and letrozole. Expression of H1047R PI3K but not E545K PI3K markedly upregulated the HER3/HER4 ligand heregulin (HRG) (Chakrabarty et al (2010) Oncogene 29(37):5193-5203).

Fulvestrant (FASLODEX®, AstraZeneca, CAS Reg. No. 129453-61-8) is a drug approved for treatment of hormone receptor-positive (HR+) breast cancer patients in the US and for ER+ patients in the EU, including postmenopausal women with disease progression following anti-estrogen therapy (Kansra (2005) Mol Cell Endocrinol 239(1-2):27-36; Flemming et al (2009) Breast Cancer Res Treat. May; 115(2):255-68; Valachis et al (2010) Crit Rev Oncol Hematol. March; 73(3):220-7). Fulvestrant is an estrogen receptor antagonist with no agonist effects, which works both by down-regulating and by degrading the estrogen receptor (Croxtall (2011) Drugs 71(3):363-380). Fulvestrant is named as (7α,17β)-7-{9-[(4,4,5,5,5-pentafluoropentyl)sulfinyl]nonyl}estra-1,3,5(10)-triene-3,17-diol and has the structure:

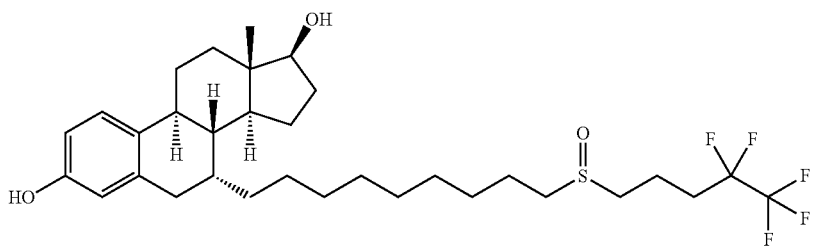

Fulvestrant belongs to a class of reversible steroidal ER antagonists that directly competes with estrogen for ER binding and is devoid of the partial agonist properties of tamoxifen. Upon binding to ER, it blocks estrogen signaling and increases the degradation of ER protein. The affinity of fulvestrant for the ER is approximately 100-fold greater than that of tamoxifen (Howell et al. (2000) Cancer 89:817-25). Like SERMs, fulvestrant attaches to the estrogen receptor and functions as an estrogen antagonist. However, unlike SERMs, fulvestrant has no estrogen agonist effects. It is a pure anti-estrogen. In addition, when fulvestrant binds to the estrogen receptor, the receptor is targeted for destruction.

Fulvestrant (250 mg once monthly) was approved by the FDA in 2002 and by the EMA in 2004 for the treatment of HR-positive MBC in postmenopausal women with disease progression following anti-estrogen therapy. In multicenter Phase III studies, fulvestrant was found to be at least equivalent to anastrozole (a non-steroidal AI) in the second-line setting (Howell et al. (2002) J Clin Oncol 20:3396-403; Osborne et al. (2002) J Clin Oncol 20:3386-95). Fulvestrant is also as active as tamoxifen for the first-line treatment of advanced breast cancer (Howell et al. (2004) J Clin Oncol 22:1605-13) and displays a level of activity in patients in the post-AI metastatic disease setting similar to that of the non-steroidal AI exemestane (Chia et al. (2008) J Clin Oncol 26:1664-70). High-dose fulvestrant (500 mg once monthly) has been demonstrated to be at least as effective as anastrozole in terms of clinical benefit rate and overall response rate and to be associated with significantly longer time to progression for the first-line treatment of women with advanced HR-positive breast cancer (Robertson et al. (2009) J Clin Oncol 27:4530-5). High-dose fulvestrant recently demonstrated superior progression-free survival (PFS) in women with ER-positive advanced breast cancer treated with 500 mg versus patients treated with 250 mg (Di Leo et al. (2010)

J Clin Oncol 28:4594-600). Fulvestrant (250 mg and 500 mg) was well tolerated in these studies and produced fewer estrogenic effects than did tamoxifen and resulted in less arthralgia than did the AI anastrozole (Osborne et al. (2002) J Clin Oncol 20:3386-95). These results led to the approval of 500 mg fulvestrant given once a month as the currently approved recommended dose in the United States and the European Union (in 2010) for postmenopausal women whose disease has spread after treatment with an AI. These studies demonstrate that fulvestrant is an important treatment option for patients with advanced breast cancer and, as such, is considered appropriate control therapy for the present study.

Letrozole (FEMARA®, Novartis Pharm.) is an oral non-steroidal aromatase inhibitor for the treatment of hormonally-responsive breast cancer after surgery (Bhatnagar et al (1990) J. Steroid Biochem. and Mol. Biol. 37:1021; Lipton et al (1995) Cancer 75:2132; Goss, P. E. and Smith, R. E. (2002) Expert Rev. Anticancer Ther. 2:249-260; Lang et al (1993) The Journal of Steroid Biochem. and Mol. Biol. 44 (4-6):421-8; EP 236940; U.S. Pat. No. 4,978,672). FEMARA® is approved by the FDA for the treatment of local or metastatic breast cancer that is hormone receptor positive (HR+) or has an unknown receptor status in post-menopausal women. Letrozole is named as 4,4'-((1H-1,2,4-triazol-1-yl)methylene)dibenzonitrile (CAS Reg. No. 112809-51-5), and has the structure:

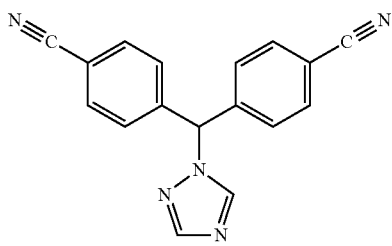 [SMILES: N#Cc1ccc(C(c2ccc(C#N)cc2)n2cncn2)cc1]

Tamoxifen (NOLVADEX®, ISTUBAL®, VALODEX®) is an orally active, selective estrogen receptor modulator (SERM) which is used in the treatment of breast cancer. Tamoxifen was first approved by the FDA (NOLVADEX®, ICI Pharmaceuticals, now AstraZeneca) in 1977 for treatment of metastatic breast cancer (Jordan V C (2006) Br J Pharmacol 147 (Suppl 1): S269-76). Tamoxifen is an antagonist of the estrogen receptor in breast tissue via its active metabolite, hydroxytamoxifen. In other tissues such as the endometrium, it behaves as an agonist, and thus may be characterized as a mixed agonist/antagonist (New Engl. J. Med. (2009) 361:766 Aug. 20, 2009). Tamoxifen is the usual endocrine (anti-estrogen) therapy for hormone receptor-positive breast cancer in pre-menopausal women, and is also a standard in post-menopausal women although aromatase inhibitors are also frequently used in that setting. Tamoxifen is currently used for the treatment of both early and advanced estrogen receptor (ER) positive breast cancer in pre- and post-menopausal women (Jordan V C (1993) Br J Pharmacol 110 (2): 507-17). It is also approved by the FDA for the prevention of breast cancer in women at high risk of developing the disease and for the reduction of contralateral (in the opposite breast) breast cancer. Tamoxifen is named as (Z)-2-[4-(1,2-diphenylbut-1-enyl)phenoxy]-N,N-dimethylethanamine (CAS Reg. No. 10540-29-1), and has the structure:

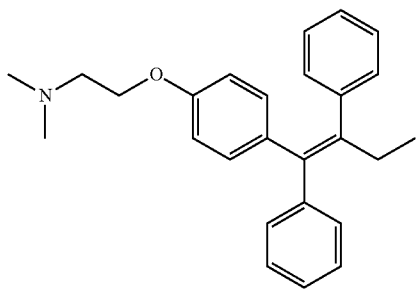 [SMILES: CC/C(=C(\c1ccccc1)c1ccc(OCCN(C)C)cc1)c1ccccc1]

Clinical Trial

A multicenter, international, randomized, double-blinded, placebo-controlled, Phase II trial was conducted for patients with advanced or metastatic ER+ breast cancer (MBC) who have previously received treatment with an aromatase inhibitor and experienced recurrence or progression while receiving AI (aromatase inhibitor) therapy.

A trial was designed to evaluate whether the addition of PI3K pathway inhibition with GDC-0941 can prolong PFS when added to fulvestrant in postmenopausal women with HR-positive MBC who have progressed on AI therapy. See Example 1. In vitro and in vivo breast cancer models harboring mutations in PIK3CA are generally sensitive to GDC-0941 (O'Brien et al. (2010) Clin Cancer Res 16:3670-83).

Study Objectives

Evaluate the efficacy as measured by PFS of fulvestrant+GDC-0941 versus fulvestrant+placebo in all treated patients Evaluate the efficacy as measured by PFS of fulvestrant+GDC-0941 versus fulvestrant+placebo in patients with and without PIK3CA mutations Evaluate the safety of fulvestrant+GDC-0941 versus fulvestrant+placebo, with focus on National Cancer Institute Common Terminology Criteria for Adverse Events Version 4.0 (NCI CTCAE v4.0) Grade 3 and 4 adverse events (AEs), serious AEs (SAES), and laboratory abnormalities Assess the clinical activity as measured by response rate, duration of response, clinical benefit rate (CBR), and OS of fulvestrant+GDC-0941 in all treated patients and in patients with and without PIK3CA mutations and/or PTEN loss Assess the predictive and prognostic effects of PIK3CA mutations and PTEN loss on PFS, response rate, and OS in patients treated with fulvestrant+GDC-0941, and fulvestrant+placebo Assess the pharmacokinetic (PK) parameters (AUC0-last, Cmax, Cmin) of GDC-0941 when administered with fulvestrant Assess the potential relationship between PK parameters of GDC-0941 and tumor response Explore fulvestrant single-point concentrations with and without administration of GDC-0941

Explore the relationship between pharmacogenetic differences in drug-metabolizing enzymes and transporters and other patient-specific covariates with PK of GDC-0941 when administered with fulvestrant Identify potential novel predictive biomarkers of treatment response through additional molecular characterization of patient samples Compare the differences in health-related quality of life (HRQL) and pain symptoms for patients by treatment assignment Study Outcome

TABLE 1

Patient and Tumor Characteristics at Baseline

| | GDC-0941 (n = 89) | Placebo (n = 79) |
|---|---|---|
| Age (years) | 89 | 79 |
| Median (Range) | 60.0 (36-90) | 63.0 (40-62) |
| ≥65 | 29 (33%) | 29 (37%) |
| Race, n | 89 | 79 |
| White | 78 (88%) | 68 (86%) |
| Asian | 5 (6%) | 8 (10%) |
| Black | 2 (2%) | 1 (1%) |
| Other | 4 (4%) | 2 (1%) |
| ECOG PS, n | 88 | 77 |
| 0 | 60 (68%) | 44 (57%) |
| 1 | 28 (32%) | 33 (43%) |
| PIK3CA Mutation Status, n | 89 | 79 |
| Mutation not detected | 45 (51%) | 39 (49%) |
| Positive | 38 (43%) | 32 (41%) |
| Status unknown | 6 (7%) | 8 (10%) |
| PIK3CA-mutation positive, n | 89 | 79 |
| Kinase domain | 20 (22%) | 22 (28%) |
| Helical domain | 18 (20%) | 11 (14%) |
| PR, n | 89 | 79 |
| Negative | 21 (24%) | 14 (18%) |
| Positive | 58 (65%) | 58 (73%) |
| Status unknown | 10 (11%) | 7 (9%) |
| Endocrine resistance, n | 89 | 79 |
| Primary | 38 (43%) | 30 (38%) |
| Secondary | 48 (54%) | 43 (54%) |
| Measuable disease (derived), n | 89 | 79 |
| Measurable | 51 (57%) | 43 (54%) |
| Non-measurable | 38 (43%) | 36 (46%) |
| Visceral disease, n | 89 | 78 |
| No | 38 (43%) | 39 (50%) |
| Yes | 51 (57%) | 39 (50%) |
| Bone only disease, n | 89 | 79 |
| No | 70 (79%) | 62 (78%) |
| Yes | 19 (21%) | 17 (22%) |
| No. of metastatic sites | 89 | 79 |
| 1 | 31 (35%) | 27 (34%) |
| 2 | 34 (38%) | 25 (32%) |
| ≥3 | 24 (27%) | 27 (34%) |
| Purpose of most recent systemic therapy, n | 89 | 78 |
| Adjuvant | 27 (30%) | 20 (26%) |
| Advanced/Metastatic | 62 (70%) | 58 (74%) |
| Previous chemotherapy, n | 89 | 79 |
| Yes | 64 (72%) | 49 (62%) |
| Neo- or adjuvant | 43 (48%) | 35 (44%) |
| Metastatic | 21 (24%) | 14 (18%) |
| No. of prior systemic regimens, n | 89 | 78 |
| 1 | 17 (19%) | 23 (29%) |
| 2 | 22 (25%) | 13 (17%) |
| ≥3 | 50 (56%) | 42 (54%) |
| No prior systemic regimens for MBC, n | 89 | 78 |
| 0 | 26 (29%) | 20 (26%) |
| 1 | 33 (37%) | 39 (50%) |
| ≥2 | 30 (34%) | 19 (24%) |

TABLE 2

Patient Disposition

| | GDC-0941 (n = 89) | Placebo (n = 79) |
|---|---|---|
| Discontinued GDC-0941/placebo | 67 (75%) | 51 (65%) |
| Disease progression | 39 (44%) | 41 (52%) |
| Non-PD | 28 (31%) | 10 (13%) |
| Adverse Events | 16 (18%) | 2 (3%) |
| Protocol-violation | 0 (0%) | 1 (1%) |
| Withdrawal by subject | 5 (6%) | 2 (3%) |
| Physician Decision | 6 (7%) | 4 (5%) |
| Other | 1 (1%) | 1 (1%) |
| Discontinued fulvestrant for non-PD | 15 (17%) | 10 (13%) |

TABLE 3

Adverse Events Irrespective of Relationship to Study Treatment in ≥10% of the GDC-0941-Fulvestrant Group

| | GD-0941 (n = 89) | | Placebo (n = 79) | |
|---|---|---|---|---|
| Adverse Event | All Grades | Grade ≥3 | All Grades | Grade ≥3 |
| Diarrhea | 58 (65%) | 5 (6%) | 12 (15%) | — |
| Nausea | 48 (54%) | 2 (2%) | 23 (29%) | — |
| Rash* | to be updated | to be updated | to be updated | to be updated |
| Fatigue | 36 (40%) | 5 (6%) | 25 (32%) | — |
| Dysgeusia | 35 (39%) | — | 3 (4%) | — |
| Vomiting | 24 (27%) | 2 (2%) | 8 (10%) | 1 (1%) |
| Decreased appetite | 20 (23%) | 1 (1%) | 9 (11%) | — |
| Stomatitis | 16 (18%) | 2 (2%) | 1 (1%) | — |
| Hyperglycemia | 16 (18%) | 4 (5%) | 4 (5%) | — |
| Constipation | 14 (16%) | — | 11 (14%) | — |
| Headache | 12 (14%) | 1 (1%) | 8 (10%) | — |
| Cough | 14 (15%) | — | 12 (15%) | — |
| Hot flush | 12 (13%) | — | 10 (13%) | — |
| Pyrexia | 12 (13%) | — | 2 (3%) | — |
| Arthralgia | 11 (12%) | — | 19 (24%) | — |
| AST increased | 11 (12%) | 3 (3%) | 8 (10%) | 2 (3%) |
| Pruritus | 11 (12%) | 1 (1%) | 8 (10%) | — |
| Alopecia | 10 (11%) | — | 3 (4%) | — |
| Dyspepsia | 10 (11%) | — | 3 (4%) | — |
| Dyspneoa | 10 (11%) | — | 7 (9%) | 1 (1%) |
| Injection site pain | 10 (11%) | — | 8 (10%) | — |
| Muscle spasms | 10 (11%) | — | 3 (4%) | — |
| Abdominal pain | 9 (10%) | 2 (2%) | 2 (3%) | — |
| Dry skin | 9 (10%) | — | 2 (3%) | — |
| Mucosal inflammation | 9 (10%) | — | 2 (3%) | — |
| Urinary tract infection | 9 (10%) | — | 4 (5%) | — |

Figure 3A:
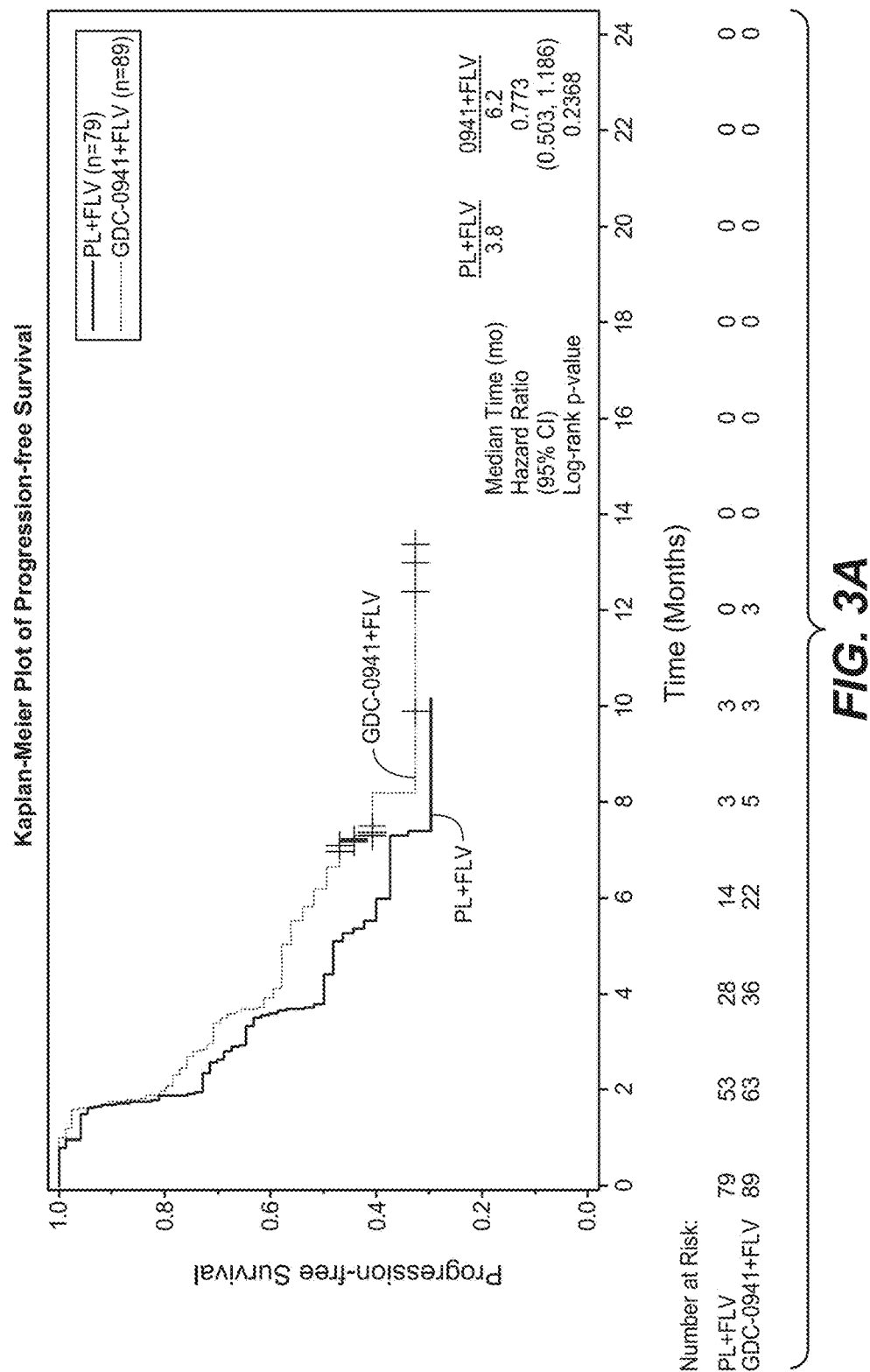
FIG. 3A shows a Kaplan-Meier Plot of Progression-free Survival in the intent to treat (ITT) study (Example 1). Hazard ratio is estimated based on unstratified Cox model; p-value is estimated based on unstratified log-rank test.
Figure 3B:
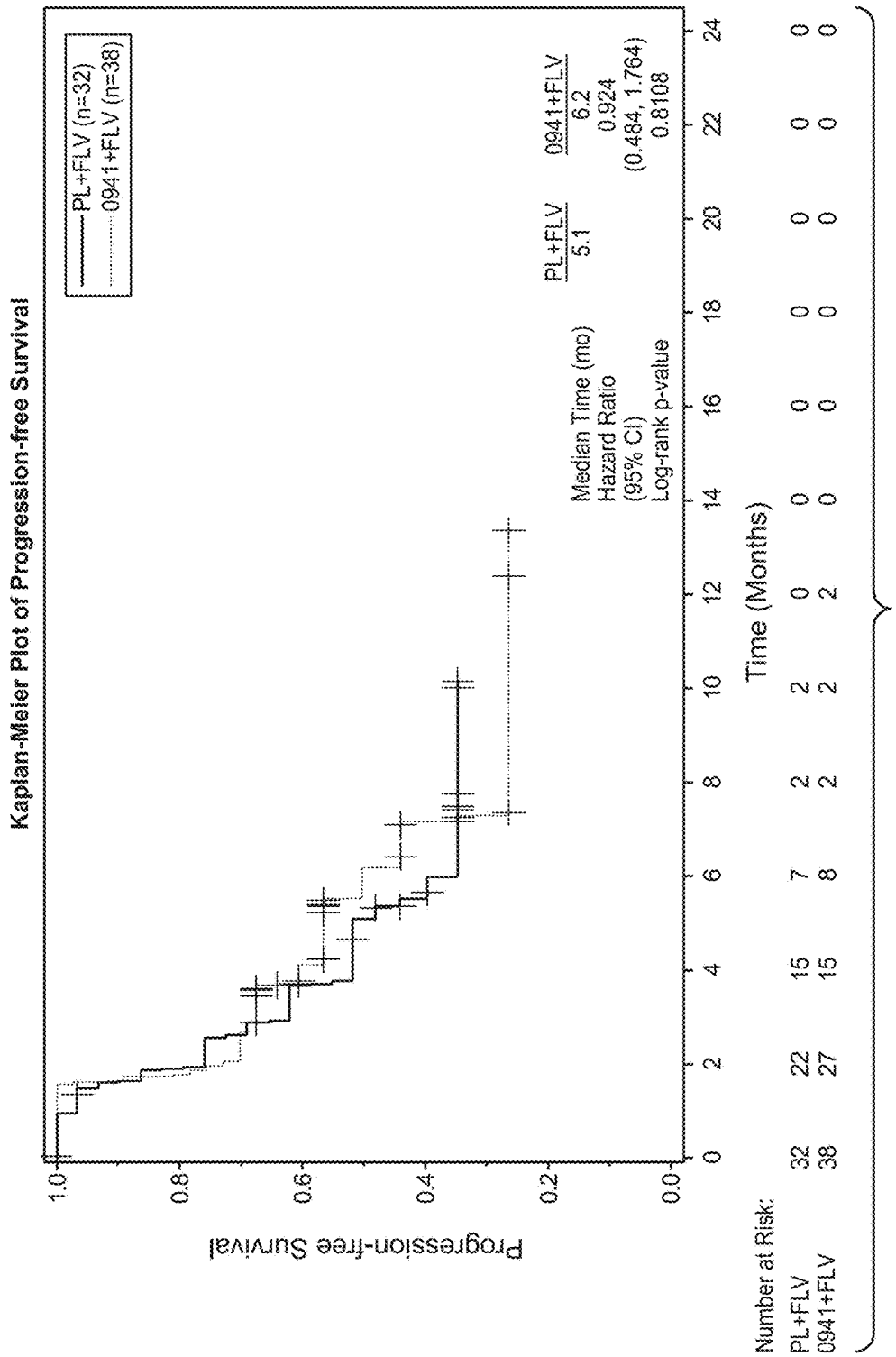
FIG. 3B shows a Kaplan-Meier Plot of Progression-free Survival
Figure 3C:
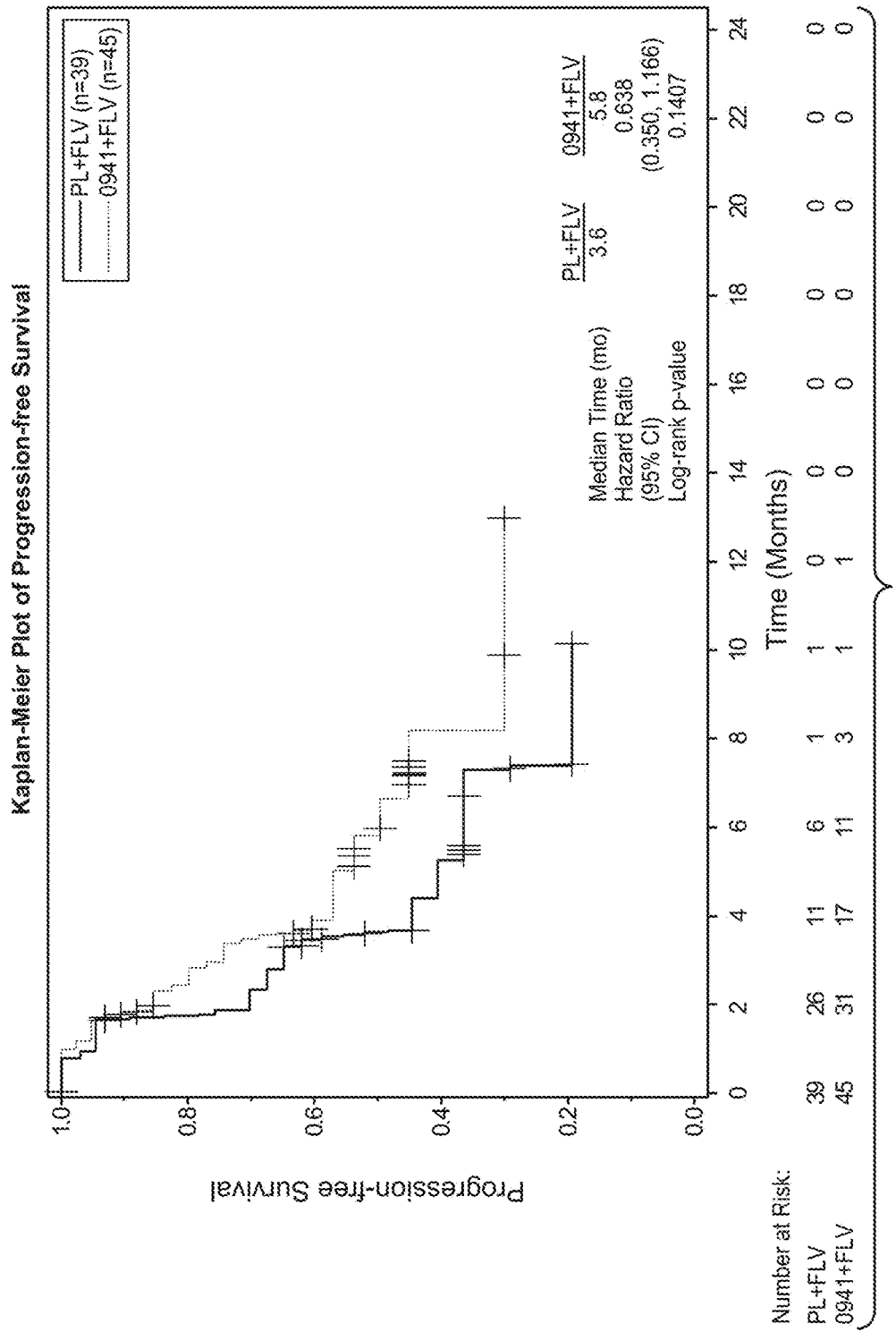
FIG. 3C shows a Kaplan-Meier Plot of Progression-free Survival

FIGS. 3A-C shows Kaplan-Meier Plots of Progression-free Survival. Population: GDC-0941 and Placebo GDC-0941 ITT (Intention-to-treat) Patients. Hazard ratio is estimated based on unstratified Cox model; p-value is estimated based on unstratified log-rank test. Benefit is maintained in all of the PR+(progesterone-receptor positive) patient populations assessed in nearly all of the patient subgroups examined indicating that a PR+ patient population may derive substantial benefit from the regimen of treatment with GDC-0941 and fulvestrant.

TABLE 4

Analysis of Progression-free Survival across various subgroups

| Baseline Risk Factors | Total n | PL0941_GDC0941 (N = 79) n | Median (Months) | GDC0941 (N = 89) n | Median (Months) | Hazard Ratio | 95% Wald CI |
|---|---|---|---|---|---|---|---|
| All Patients | 168 | 79 | 3.8 | 89 | 6.2 | 0.77 | (0.50, 1.19) |
| PIK3CA Mutation Status | | | | | | | |
| Positive | 70 | 32 | 5.1 | 38 | 6.2 | 0.92 | (0.48, 1.76) |
| Wild Type | 84 | 39 | 3.6 | 45 | 5.8 | 0.64 | (0.35, 1.17) |
| Unknown | 14 | 8 | NE | 6 | NE | 1.31 | (0.18, 9.40) |
| PIK3CA Helical Domain Mutation Status | | | | | | | |
| Positive | 30 | 11 | 5.5 | 19 | 7.3 | 1.16 | (0.38, 3.53) |
| Wild Type | 119 | 55 | 3.7 | 64 | 6.2 | 0.64 | (0.39, 1.06) |
| Unknown | 19 | 13 | 6.0 | 6 | NE | 1.17 | (0.28, 4.91) |
| PIK3CA Kinase Domain Mutation Status | | | | | | | |
| Positive | 42 | 22 | 3.7 | 20 | 6.2 | 0.68 | (0.30, 1.54) |
| Wild Type | 118 | 53 | 4.4 | 65 | 6.6 | 0.80 | (0.47, 1.35) |
| Unknown | 8 | 4 | NE | 4 | NE | 1.95 | (0.17, 21.95) |
| Primary/Secondary Resistance (Derived) | | | | | | | |
| Primary Resistance | 68 | 30 | 3.7 | 38 | 5.0 | 0.71 | (0.39, 1.31) |
| Secondary Resistance | 91 | 43 | 7.3 | 48 | NE | 0.75 | (0.39, 1.46) |
| Unknown | 9 | 6 | 2.3 | 3 | 1.7 | >999.99 | (0.00, NE) |
| Visceral Disease | | | | | | | |
| Yes | 90 | 39 | 2.9 | 51 | 4.1 | 0.68 | (0.39, 1.17) |
| No | 77 | 39 | 7.3 | 38 | 8.2 | 0.69 | (0.32, 1.48) |

TABLE 5

Analysis of Progression-free Survival across various subgroups

| Baseline Risk Factors | Total n | PL0941_GDC0941 (N = 79) n | Median (Months) | GDC0941 (N = 89) n | Median (Months) | Hazard Ratio | 95% Wald CI |
|---|---|---|---|---|---|---|---|
| All Patients | 168 | 79 | 3.8 | 89 | 6.2 | 0.77 | (0.50, 1.19) |
| Received Prior Adjuvant/Neo-Adjuvant Therapy | | | | | | | |
| Yes | 119 | 54 | 3.7 | 65 | 7.2 | 0.66 | (0.40, 1.08) |
| No | 48 | 24 | 7.3 | 24 | 4.1 | 1.33 | (0.55, 3.22) |
| Num of Previous Therapies in Metastatic Setting | | | | | | | |
| 0 | 46 | 20 | 3.7 | 26 | 6.6 | 0.46 | (0.21, 1.01) |
| 1 | 72 | 39 | 7.3 | 33 | 6.2 | 1.11 | (0.54, 2.24) |
| 2 | 31 | 10 | 5.4 | 21 | NE | 0.88 | (0.29, 2.70) |
| 3+ | 18 | 9 | 2.8 | 9 | 3.6 | 0.55 | (0.17, 1.76) |
| Measurable Disease at Baseline (Derived) | | | | | | | |
| Yes | 94 | 43 | 3.8 | 51 | 5.0 | 1.11 | (0.63, 1.92) |
| No | 74 | 36 | 4.4 | 38 | NE | 0.45 | (0.22, 0.93) |
| Bone Only Non-Measureable Disease at Baseline | | | | | | | |
| Yes | 36 | 17 | 4.7 | 19 | NE | 0.23 | (0.06, 0.84) |
| No | 132 | 62 | 3.8 | 70 | 5.0 | 0.94 | (0.59, 1.51) |

TABLE 5-continued

Analysis of Progression-free Survival across various subgroups

| | | PL0941_GDC0941 (N = 79) | | GDC0941 (N = 89) | | | |
|---|---|---|---|---|---|---|---|
| Baseline Risk Factors | Total n | n | Median (Months) | n | Median (Months) | Hazard Ratio | 95% Wald CI |
| PR Status | | | | | | | |
| Positive | 116 | 58 | 3.7 | 58 | 7.2 | 0.45 | (0.27, 0.78) |
| Negative | 35 | 14 | 5.5 | 21 | 5.0 | 1.40 | (0.54, 3.64) |
| Status Unknown | 17 | 7 | NE | 10 | 2.9 | 7.21 | (0.88, 59.19) |
| Baseline ECOG Score | | | | | | | |
| 0 | 104 | 44 | 3.6 | 60 | 6.6 | 0.56 | (0.32, 0.96) |
| 1 | 61 | 33 | 7.4 | 28 | 5.0 | 1.41 | (0.68, 2.93) |

TABLE 6

| Subgroup | N GDC-0941/ placebo | Events GDC-0941/placebo | Median PFS GDC-0941/placebo | HR | 95% CI |
|---|---|---|---|---|---|
| PR+ | 50/52 | 19/32 | 7.16/3.68 | 0.47 | 0.27, 0.83 |
| LumA | 46/52 | 15/27 | NA/5.26 | 0.60 | 0.32, 1.12 |
| PR+, LumA | 34/39 | 9/25 | NA/3.68 | 0.31 | 0.14, 0.67 |
| PR+, LumB | 16/13 | 10/7 | 3.91/3.32 | 0.92 | 0.35, 2.43 |
| PR−, LumA | 9/7 | 3/2 | NA/NA | 1.75 | 0.29, 10.68 |

Treatment

At the cutoff date, 37 total progressive disease events occurred in the patients with a PIK3CA-mutant tumor and 84 total patients progressed in Part I of the study. At this time, the median duration of follow-up was 5.7 months with patients in the combination group and in the fulvestrant-only group continued to receive study treatment. The median duration of exposure to GDC-0941 was 11.7 weeks, as compared to 14.3 weeks of exposure for patients that received placebo. The median duration of exposure to fulvestrant was 16.0 and 16.1 weeks in the combination and fulvestrant-only groups. Progression of disease was the most frequent reason for discontinuation in the combination-therapy (44%) and fulvestrant-only groups (52%). A total of 28 (31%) and 10 (13%) of the patients discontinued the oral agent (GDC-0941 or placebo) for events unrelated to disease progression in the combination-therapy and fulvestrant-only groups, respectively. Pharmacokinetic analyses demonstrated that fulvestrant exposure is similar across all of the primary patient subgroups and the observed GDC-0941 exposure could be well predicted by the GDC-0941 popPK model developed using Phase I data (data not shown).

Efficacy

Figure 4:
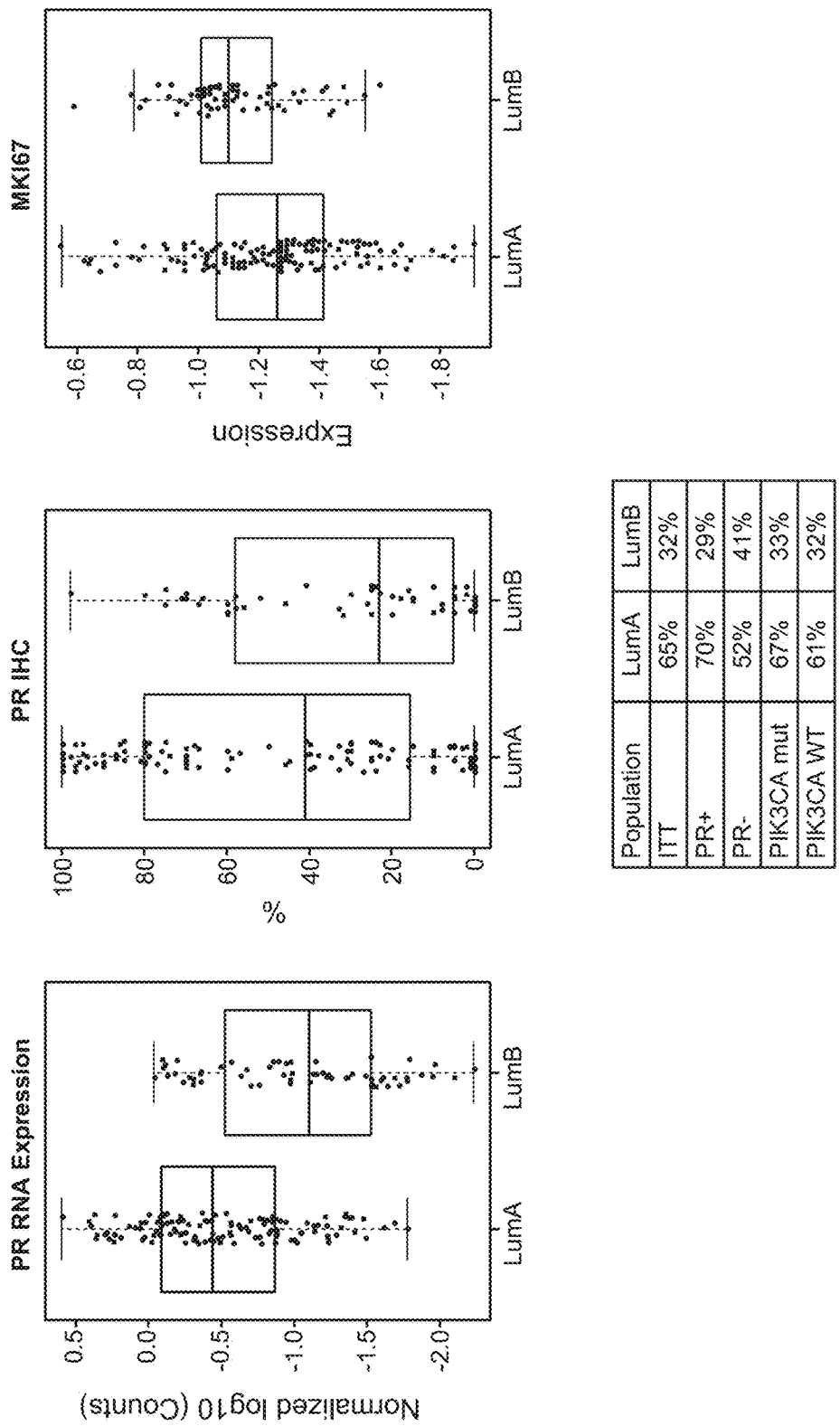
FIG. 4 shows the prevalence of luminal A and luminal B PAM50 intrinsic subtypes from the patients enrolled on to the study, and association with relevant biomarkers
Figure 5A:
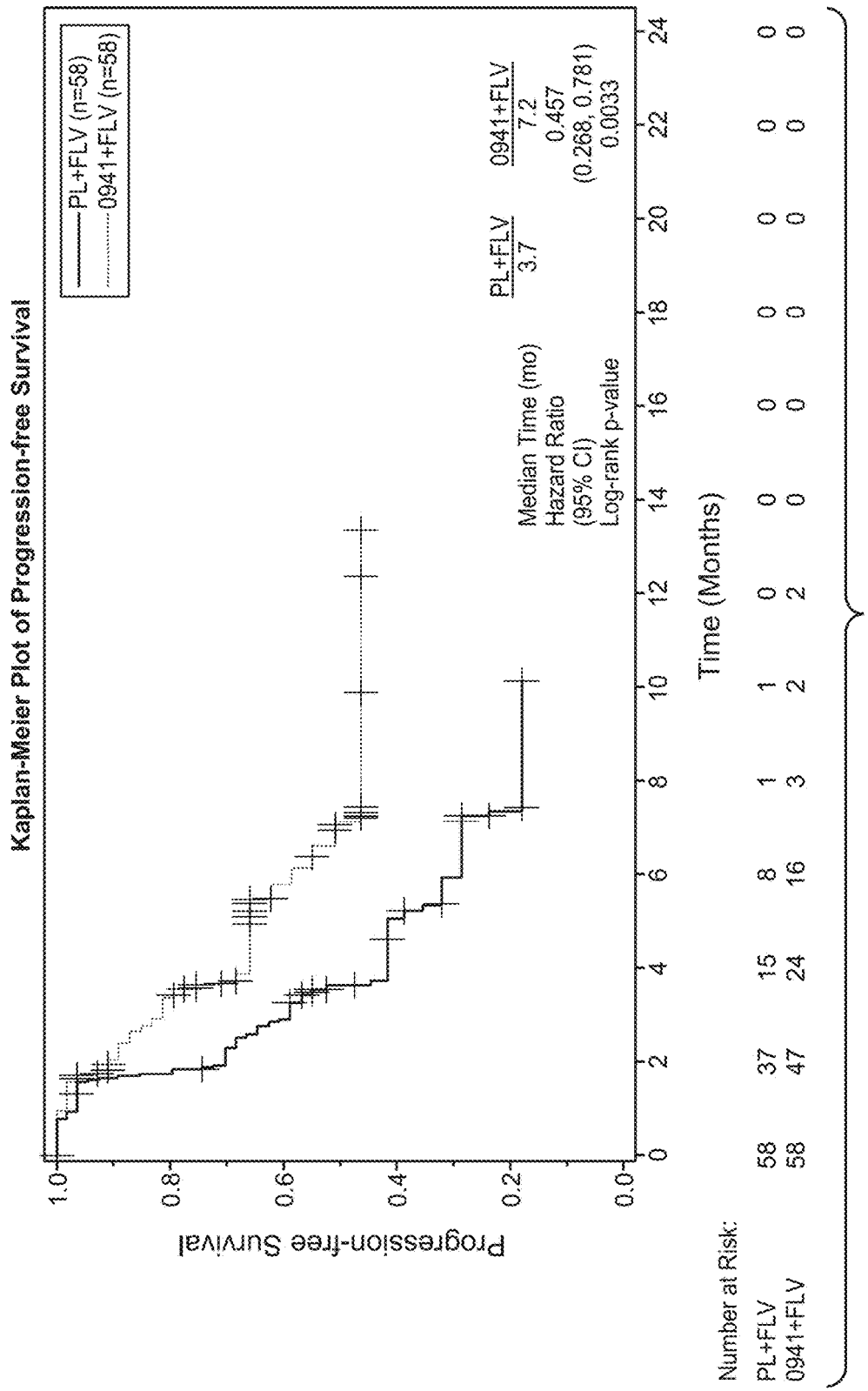
FIG. 5A shows a Kaplan-Meier Plot of Progression-free Survival in PR-positive subgroups
Figure 5B:
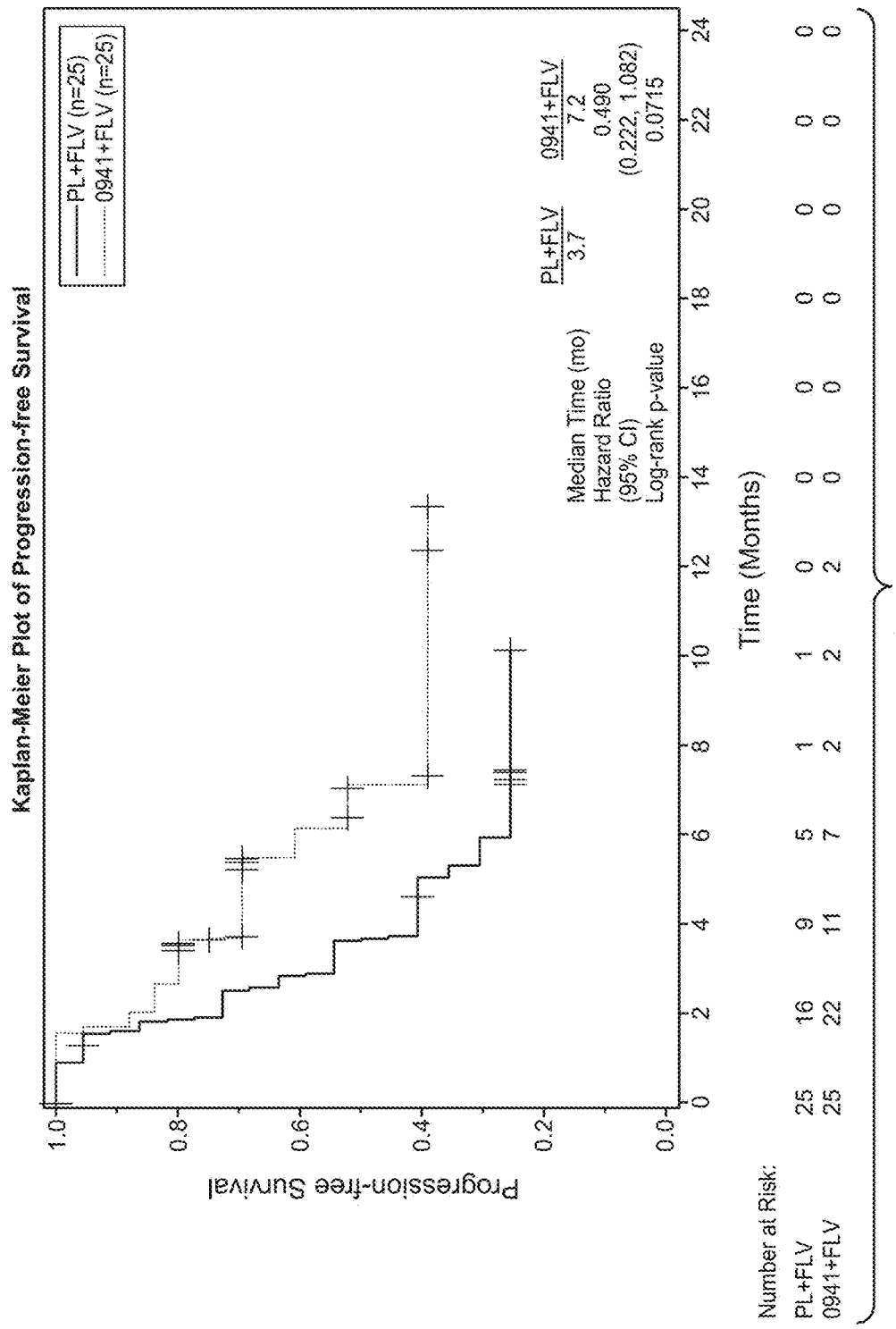
FIG. 5B shows a Kaplan-Meier Plot of Progression-free Survival in PR-positive subgroups
Figure 5C:
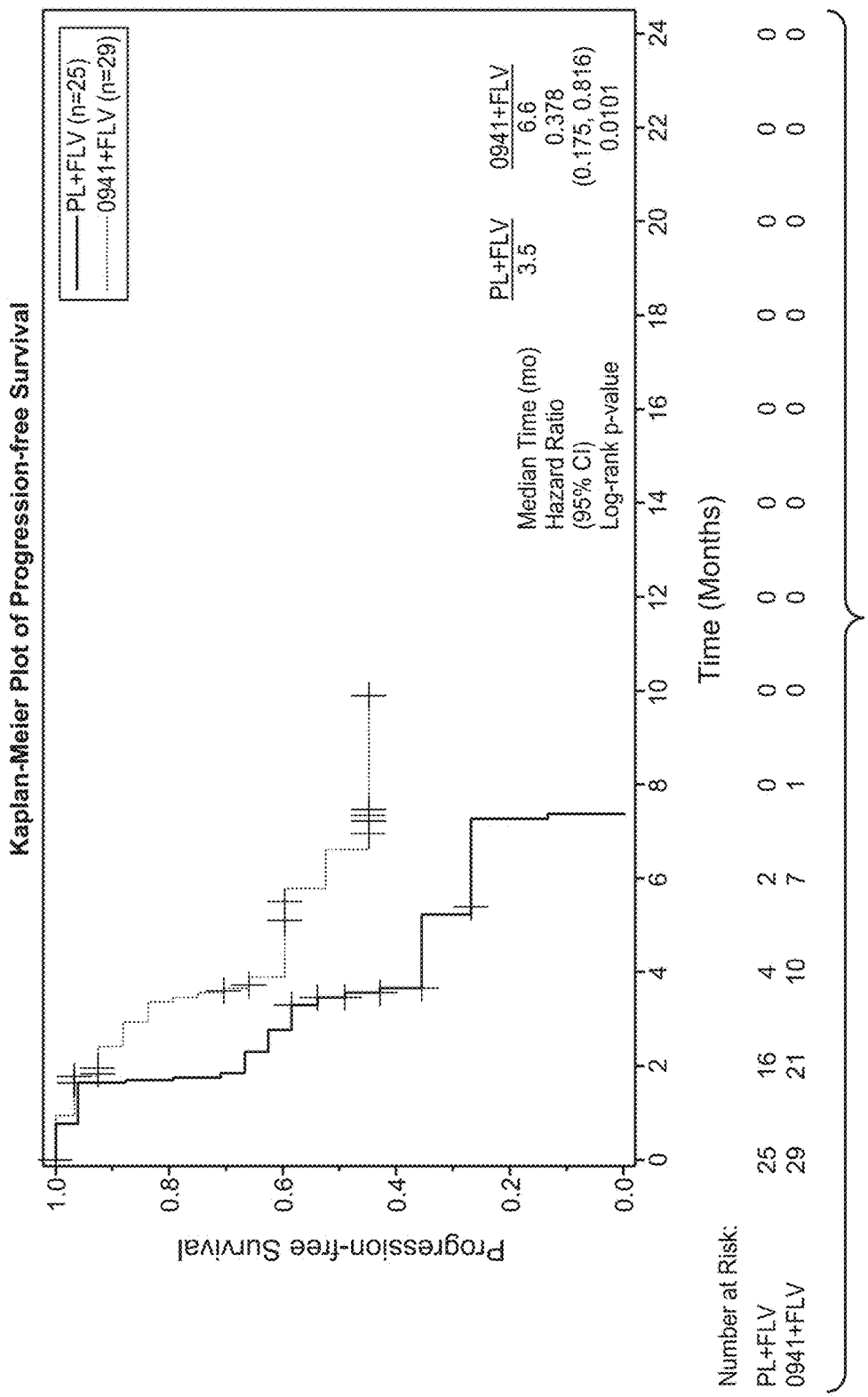
FIG. 5C shows a Kaplan-Meier Plot of Progression-free Survival in PR-positive subgroups

In the intend-to-treat population (N=168; 84 PFS events) the median progression-free survival (PFS), on the basis of radiographic studies assessed by the local investigators, was 6.3 months for GDC-0941 plus fulvestrant versus 3.8 months for placebo plus fulvestrant (hazard ratio, 0.77; 95% confidence interval [CI], 0.50 to 1.19; P=0.24). See FIG. 3A. For patients with a detectable PIK3CA-mutant tumor (n=70; 34 PFS events), the median PFS was 6.2 months for GDC-0941 plus fulvestrant versus 5.1 months for placebo plus fulvestrant (hazard ratio for progression or death, 0.92; 95% CI, 0.48 to 1.76; P=0.81) and the 95% CIs of the PFS HR for patients with helical- and kinase-domain mutations were largely overlapping. See FIG. 3B. For patients without a detectable PIK3CA-mutant tumor (n=70; 34 PFS events), the median PFS 5.8 months for GDC-0941 plus fulvestrant versus 3.6 months for placebo plus fulvestrant (hazard ratio for progression or death, 0.64; 95% CI, 0.35 to 1.17; P=0.14). See FIG. 3C Exploratory subgroup analysis (Table 6) suggested a trend for an improvement in PFS patients with good performance status (0 versus 1), bone-only disease and those with progesterone receptor-positive (PR) tumors that received the combination therapy versus the patient that received fulvestrant only. In the PR-positive subgroup (n=116, representing 70% of the ITT; 57 PFS events) the median PFS was 7.2 months for GDC-0941 plus fulvestrant versus 3.7 months for placebo plus fulvestrant (hazard ratio for progression or death, 0.46; 95% CI, 0.27 to 0.78; P=0.0042; test for interaction, P=0.035; FIG. 3A). Given that PR expression is correlated with Luminal A subtype (Prat, 2013), patient samples were classified into intrinsic subtypes with 50-gene predictor (PAM50) by the quantitative reverse transcriptase PCR (qRT-PCR). As expected, of the 151 patient samples that were assessed by this assay, the majority were classified as either Luminal A or Luminal B, with an enrichment of Luminal A tumors in the PR-positive subgroup (FIG. 4). In the Luminal A-positive subgroup (n=98, representing 65% of the ITT; 42 PFS events) the median PFS was not reached for GDC-0941 plus fulvestrant versus 5.26 months for placebo plus fulvestrant (hazard ratio for progression or death, 0.60; 95% CI, 0.32 to 1.12; P=0.11; test for interaction, P=0.23). This possible improvement in the combination therapy in these two subgroups (i.e., patients with PR-positive or Luminal A tumors) was independent of tumor PIK3CA-mutation status. Further exploratory analyses of patients whose tumors were both PR-positive and Luminal A subtype (n=73, representing 43% of the ITT; 34 PFS events), the combination therapy the median PFS was not reached for versus 5.7 months for placebo plus fulvestrant (hazard ratio for progression or death, 0.31; 95% CI, 0.14, 0.67). Table 8 shows a summary of PFS Analyses in the ITT, PR and Luminal A/B Subgroups.

TABLE 8

Summary of PFS Analyses in the ITT, PR and Luminal A/B Subgroups

|  |  | ITT | PR-Positive | PR-Negative | LumA | LumB | PR-Positve; LumA |
|---|---|---|---|---|---|---|---|
| Patients | N | 168 | 116 | 35 | 98 | 48 | 73 |
| PFS events | N | 84 | 57 | 18 | 42 | 30 | 34 |
| Placebo | N | 79 | 58 | 14 | 52 | 20 | 39 |
|  | Median PFS | 3.8 | 3.7 | 5.5 | 5.3 | 3.6 | 3.7 |
| GDC-0941 | N | 89 | 58 | 21 | 46 | 28 | 34 |
|  | Median PFS | 6.2 | 7.2 | 5 | NA | 3.7 | NA |
|  | HR | 0.77 | 0.46 | 1.40 | 0.60 | 1.05 | 0.31 |
|  | 95% CI | 0.5, 1.19 | 0.27, 0.78 | 0.54, 3.64 | 0.32, 1.12 | 0.51, 2.19 | 0.14, 0.67 |

Multivariate analysis of the PR-positive and Luminal A subgroup suggested that the treatment effect is maintained after adjusting for possible baseline imbalances (Table 9).

TABLE 9

Multivariate Analysis of the PR-Positive and Luminal A Subgroups

|  | ITT | PR-positive | Luminal A |
|---|---|---|---|
| Unstratified analysis | 0.77 (0.5, 1.19) | 0.46 (0.27, 0.78) | 0.6 (0.32, 1.12) |
| Stratified analysis |  |  |  |
| PIK3CA mut, endocrine resistance, measurable disease | 0.73 (0.45, 1.16) | 0.48 (0.26, 0.87) | 0.56 (0.28, 1.13) |
| PIK3CA mut, endocrine resistance, measurable, disease, age, ECOG, BOLERO resistance, bone-only, visceral disease, last therapy setting, metastatic chemo | 0.59 (0.19, 1.87) | 0.33 (0.06, 1.69) | 0.41 (0.1, 1.64) |
| PIK3CA mutation, endocrine resistance, visceral disease | 0.62 (0.39, 1) | 0.38 (0.2, 0.72) | 0.54 (0.27, 1.06) |
| PIK3CA mutation, endocrine resistance, visceral disease, PR status, Luminal A/B | 0.55 (0.29, 1.05) | 0.42 (0.2, 0.87) | 0.45 (0.22, 0.93) |

Response rates, on the basis of local assessment, were 7% and 5% in the combination-therapy and fulvestrant-alone groups, respectively. There were a numerically greater number of patients that experience a response with a PIK3CA-mutant tumors treated in the combination-therapy arm than patients that received fulvestrant-only (13% versus 3%). The response rate for patients without a detectable PIK3CA-mutant tumor was 2% and 5% in the combination-therapy and fulvestrant-only populations, respectively.

FIG. 6 shows a Kaplan-Meier Plot of Progression-free Survival by luminal subgroups. Luminal B patients treated with GDC-0941+fulvestrant or placebo were compared with Luminal A patients treated with GDC-0941+fulvestrant or placebo. The Luminal A subtype patient population appears prognostic and predictive of benefit with the combination of GDC-0941 and fulvestrant. Table 10 shows the scoring of the FIG. 6 plot.

TABLE 10

| Subgroup | N GDC-0941/placebo | Events GDC-0941/placebo | Median PFS GDC-0941/placebo | HR | 95% CI |
|---|---|---|---|---|---|
| All | 74/72 | 33/39 | 6.18/5.09 | 0.81 | 0.51, 1.28 |
| LumA | 46/52 | 15/27 | NA/5.26 | 0.60 | 0.32, 1.12 |
| LumB | 28/20 | 18/12 | 3.71/3.55 | 1.05 | 0.51, 2.19 |

HR = hazard ratio
CI = combination index

Figure 7:
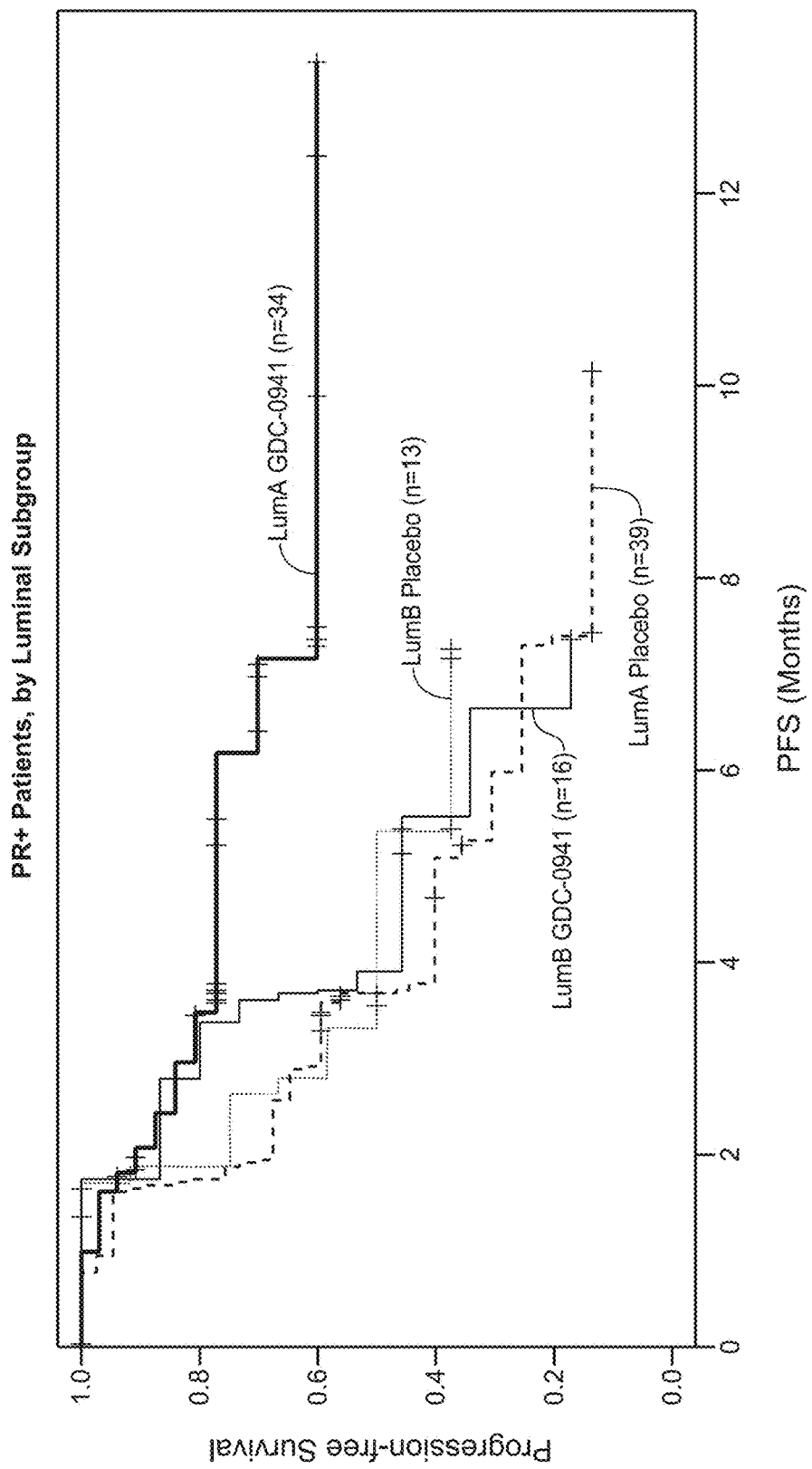
FIG. 7 shows a plot of Kaplan-Meier Plot of Progression-free Survival for PAM50 analysis in PR+ subgroup.

FIG. 7 shows a Kaplan-Meier Plot of Progression-free Survival of PR+ patients by luminal subgroup.

Figure 8:
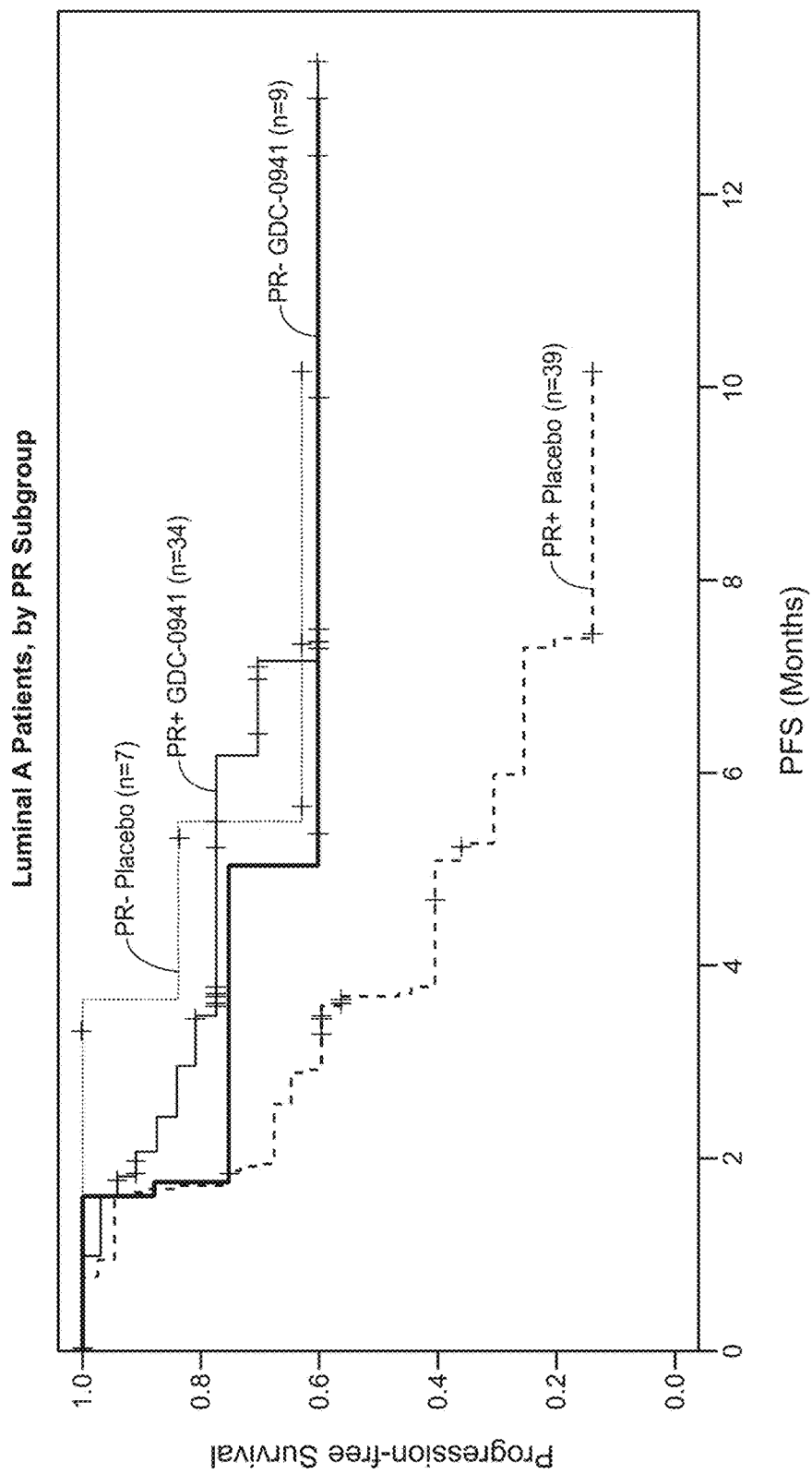
FIG. 8 shows a plot of Kaplan-Meier Plot of Progression-free Survival.

FIG. 8 shows a Kaplan-Meier Plot of Progression-free Survival of Luminal A patients, by PR subgroup.

Conclusions

GDC-0941+fulvestrant is active in ER+MBC patients that failed prior AI therapy independent of PIK3CA mutation status. GDC-0941+fulvestrant improved the median PFS of this patient group by 10.5 weeks (from 3.8 to 6.2 months in the placebo- and GDC-0941-treated groups, respectively)

The 340 mg dose of GDC-0941 in combination with fulvestrant had an acceptable tolerability profile. The rate of discontinuation for non-PD events (31%) similar to what was observed with other pathway inhibitors (BOLERO-2 and TAMRAD, 24%). Toxicity at the 340 mg dose impacted the ability of patients to receive treatment until progression (66% of the patients experienced a dose modification for an adverse event)

Exploratory analysis suggests that the PR+ subgroup benefits substantially from GDC-0941 in combination with endocrine therapy. Subgroup analyses suggest that the benefit was particularly striking in patients that were positive for both the estrogen and progesterone receptor that resulted in nearly a doubling of the median PFS and an overall improvement of over 15 weeks (from 3.7 to 7.2 months in the placebo and pictilisib-treated groups, respectively). ITT analysis was confounded by imbalance of patients with poor prognostic features, particularly in PR− subgroup, that favored placebo. PR+ may identify a population, characterized by initial endocrine sensitivity, which derives greater benefit from treatment with GDC-0941.

Pharmaceutical Compositions and Formulations

Pharmaceutical compositions or formulations of the present invention include combinations of GDC-0941 and a therapeutic agent, formulated with one or more pharmaceutically acceptable carrier, glidant, diluent, or excipient.

GDC-0941 and therapeutic agents of the present invention may exist in unsolvated as well as solvated forms with pharmaceutically acceptable solvents such as water, ethanol, and the like, and it is intended that the invention embrace both solvated and unsolvated forms.

The compounds of the present invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Pharmaceutical compositions encompass both the bulk composition and individual dosage units comprised of more than one (e.g., two) pharmaceutically active agents including GDC-0941 and a therapeutic agent selected from the lists of the additional agents described herein, along with any pharmaceutically inactive excipients, diluents, carriers, or glidants. The bulk composition and each individual dosage unit can contain fixed amounts of the aforesaid pharmaceutically active agents. The bulk composition is material that has not yet been formed into individual dosage units. An illustrative dosage unit is an oral dosage unit such as tablets, pills, capsules, and the like. Similarly, the methods of treating a patient by administering a pharmaceutical composition is also intended to encompass the administration of the bulk composition and individual dosage units.

Pharmaceutical compositions also embrace isotopically-labeled compounds of the present invention which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Certain isotopically-labeled compounds of the present invention (e.g., those labeled with $^{3}H$ and $^{14}C$) are useful in compound and/or substrate tissue distribution assays. Tritiated ($^{3}H$) and carbon-14 ($^{14}C$) isotopes are useful for their ease of preparation and detectability. Further, substitution with heavier isotopes such as deuterium ($^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy. Isotopically labeled compounds of the present invention can generally be prepared by following procedures analogous to those disclosed in the Examples herein below, by substituting an isotopically labeled reagent for a non-isotopically labeled reagent.

GDC-0941 and therapeutic agents are formulated in accordance with standard pharmaceutical practice for use in a therapeutic combination for therapeutic treatment (including prophylactic treatment) of hyperproliferative disorders in mammals including humans. The invention provides a pharmaceutical composition comprising GDC-0941 in association with one or more pharmaceutically acceptable carrier, glidant, diluent, additive, or excipient.

Suitable carriers, diluents, additives, and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), dimethylsulfoxide (DMSO), cremophor (e.g. CREMOPHOR EL®, BASF), and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, GDC-0941 having the desired degree of purity may optionally be mixed with pharmaceutically acceptable diluents, carriers, excipients or stabilizers (Remington's Pharmaceutical Sciences (1995) 18th edition, Mack Publ. Co., Easton, Pa.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8.

The pharmaceutical formulation is preferably sterile. In particular, formulations to be used for in vivo administration must be sterile. Such sterilization is readily accomplished by filtration through sterile filtration membranes.

The pharmaceutical formulation ordinarily can be stored as a solid composition, a lyophilized formulation or as an aqueous solution.

The pharmaceutical formulations of the invention will be dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

The initial pharmaceutically effective amount of GDC-0941 administered orally or parenterally per dose will be in the range of about 0.01-1000 mg/kg, namely about 0.1 to 20 mg/kg of patient body weight per day, with the typical initial range of compound used being 0.3 to 15 mg/kg/day. The dose of GDC-0941 and the dose of the therapeutic agent to be administered may range for each from about 1 mg to about 1000 mg per unit dosage form, or from about 10 mg to about 100 mg per unit dosage form. The doses of GDC-0941 compound and the therapeutic agent may be administered in a ratio of about 1:50 to about 50:1 by weight, or in a ratio of about 1:10 to about 10:1 by weight.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, CREMOPHOR EL®, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 18th edition, (1995) Mack Publ. Co., Easton, Pa.

Sustained-release preparations of GDC-0941 and therapeutic compounds may be prepared. Suitable examples of sustained-release preparations include semipermeable matrices of solid hydrophobic polymers containing GDC-0941, which matrices are in the form of shaped articles, e.g., films, or microcapsules. Examples of sustained-release matrices include polyesters, hydrogels (for example, poly (2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D (−) 3-hydroxybutyric acid.

The pharmaceutical formulations include those suitable for the administration routes detailed herein. The formulations may conveniently be presented in unit dosage form and may be prepared by any of the methods well known in the art of pharmacy. Techniques and formulations generally are found in Remington's Pharmaceutical Sciences $18^{th}$ Ed. (1995) Mack Publishing Co., Easton, Pa. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of GDC-0941 and/or therapeutic agent suitable for oral administration may be prepared as discrete units such as pills, hard or soft e.g., gelatin capsules, cachets, troches, lozenges, aqueous or oil suspensions, dispersible powders or granules, emulsions, syrups or elixirs each containing a predetermined amount of GDC-0941 and/or a therapeutic agent. The amount of GDC-0941 and the amount of therapeutic agent may be formulated in a pill, capsule, solution or suspension as a combined formulation. Alternatively, GDC-0941 and the therapeutic agent may be formulated separately in a pill, capsule, solution or suspension for administration by alternation.

Formulations may be prepared according to any method known to the art for the manufacture of pharmaceutical compositions and such compositions may contain one or more agents including sweetening agents, flavoring agents, coloring agents and preserving agents, in order to provide a palatable preparation. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablet excipients of a pharmaceutical formulation of the invention may include: Filler (or diluent) to increase the bulk volume of the powdered drug making up the tablet; Disintegrants to encourage the tablet to break down into small fragments, ideally individual drug particles, when it is ingested and promote the rapid dissolution and absorption of drug; Binder to ensure that granules and tablets can be formed with the required mechanical strength and hold a tablet together after it has been compressed, preventing it from breaking down into its component powders during packaging, shipping and routine handling; Glidant to improve the flowability of the powder making up the tablet during production; Lubricant to ensure that the tableting powder does not adhere to the equipment used to press the tablet during manufacture. They improve the flow of the powder mixes through the presses and minimize friction and breakage as the finished tablets are ejected from the equipment; Antiadherent with function similar to that of the glidant, reducing adhesion between the powder making up the tablet and the machine that is used to punch out the shape of the tablet during manufacture; Flavor incorporated into tablets to give them a more pleasant taste or to mask an unpleasant one, and Colorant to aid identification and patient compliance.

Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base.

The aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions of this invention may be constituted from known ingredients in a known manner, including a mixture of at least one emulsifier with a fat or an oil, or with both a fat and an oil. Preferably, a hydrophilic emulsifier is included together with a lipophilic emulsifier which acts as a stabilizer. Together, the emulsifier(s) with or without stabilizer(s) make up an emulsifying wax, and the wax together with the oil and fat comprise an emulsifying ointment base which forms the oily dispersed phase of cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of the pharmaceutical formulations of the invention contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Pharmaceutical compositions may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may be a solution or a suspension in a non-toxic parenterally acceptable diluent or solvent, such as a solution in 1,3-butanediol or prepared from a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

GDC-0941 may be employed in combination with endocrine therapy agents for the treatment of progesterone-receptor positive (PR+) and/or luminal A type breast cancer. In certain embodiments, GDC-0941 is combined with the endocrine therapy agent in a single formulation as a single tablet, pill, capsule, or solution for simultaneous administration of the combination. In other embodiments, GDC-0941 and the endocrine therapy agent are administered according to a dosage regimen or course of therapy in separate formulations as separate tablets, pills, capsules, or solutions for sequential administration of GDC-0941 and the endocrine therapy agent. The combination of GDC-0941 and endocrine therapy agent may have synergistic properties. The endocrine therapy agent of the pharmaceutical combination formulation or dosing regimen preferably has complementary activities to GDC-0941, and such that they do not adversely affect each other. Such compounds of the therapeutic combination may be administered in amounts that are effective for the purpose intended. In one embodiment, a pharmaceutical formulation of this invention comprises GDC-0941 and a endocrine therapy agent such as described herein. In another embodiment, the therapeutic combination is administered by a dosing regimen wherein the therapeutically effective amount of GDC-0941 is administered in a range from twice daily to once every three weeks (q3wk), and the therapeutically effective amount of the endocrine therapy agent is administered separately, in alternation, in a range from twice daily to once every three weeks.

Therapeutic combinations of the invention include a GDC-0941, and a endocrine therapy agent selected from fulvestrant and letrozole, for separate, simultaneous or sequential use in the treatment of breast cancer.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other therapeutic agents or treatments, such as to increase the therapeutic index or mitigate toxicity or other side-effects or consequences.

In a particular embodiment of anti-cancer therapy, the therapeutic combination may be combined with surgical therapy and radiotherapy, as adjuvant therapy. Combination therapies according to the present invention include the administration of GDC-0941 and one or more other cancer treatment methods or modalities. The amounts of GDC-0941 and the therapeutic agent(s) and the relative timings of administration will be selected in order to achieve the desired combined therapeutic effect.

Administration of Pharmaceutical Compositions

The therapeutic combinations of the invention may be administered by any route appropriate to the condition to be treated. Suitable routes include oral, parenteral (including subcutaneous, intramuscular, intravenous, intraarterial, inhalation, intradermal, intrathecal, epidural, and infusion techniques), transdermal, rectal, nasal, topical (including buccal and sublingual), vaginal, intraperitoneal, intrapulmonary and intranasal. Topical administration can also involve the use of transdermal administration such as transdermal patches or iontophoresis devices. Formulation of drugs is discussed in Remington's Pharmaceutical Sciences, 18$^{th}$ Ed., (1995) Mack Publishing Co., Easton, Pa. Other examples of drug formulations can be found in Liberman, H. A. and Lachman, L., Eds., Pharmaceutical Dosage Forms, Marcel Decker, Vol 3, 2$^{nd}$ Ed., New York, N.Y. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier, glidant, or excipient. Where the compound is administered parenterally, it may be formulated with a pharmaceutically acceptable parenteral vehicle or diluent, and in a unit dosage injectable form, as detailed below.

A dose to treat human patients may range from about 1 mg to about 1000 mg of GDC-0941, such as about 5 mg to about 20 mg of the compound. A dose may be administered once a day (QD), twice per day (BID), or more frequently, depending on the pharmacokinetic (PK) and pharmacodynamic (PD) properties, including absorption, distribution, metabolism, and excretion of the particular compound. In addition, toxicity factors may influence the dosage and administration dosing regimen. When administered orally, the pill, capsule, or tablet may be ingested twice daily, daily or less frequently such as weekly or once every two or three weeks for a specified period of time. The regimen may be repeated for a number of cycles of therapy.

Methods of Treatment

The methods of the invention include:

Methods of diagnosis based on the identification of a biomarker;

Methods of determining whether a patient will respond to GDC-0941, or a combination of GDC-0941 and an endocrine therapy agent;

Methods of optimizing therapeutic efficacy by monitoring clearance of GDC-0941, or a combination of GDC-0941 and an endocrine therapy agent;

Methods of optimizing a therapeutic regime of GDC-0941, or a combination of GDC-0941 and an endocrine therapy agent, by monitoring the development of therapeutic resistance mutations; and Methods for identifying which patients will most benefit from treatment with GDC-0941 or a combination of GDC-0941 and an endocrine therapy agent therapies and monitoring patients for their sensitivity and responsiveness to treatment with GDC-0941 or a combination of GDC-0941 and an endocrine therapy therapies.

The methods of the invention are useful for inhibiting abnormal cell growth or treating a hyperproliferative disorder such as cancer in a mammal (e.g., human). For example, the methods are useful for diagnosing, monitoring, and treating multiple myeloma, lymphoma, leukemias, prostate cancer, breast cancer, hepatocellular carcinoma, pancreatic cancer, and/or colorectal cancer in a mammal (e.g., human).

Therapeutic combinations of: (1) GDC-0941 and (2) an endocrine therapy agent are useful for treating diseases, conditions and/or disorders including, but not limited to, those characterized by activation of the PI3 kinase pathway. Accordingly, another aspect of this invention includes methods of treating diseases or conditions that can be treated by inhibiting lipid kinases, including PI3. In one embodiment, a method for the treatment of a solid tumor or hematopoietic malignancy comprises administering a therapeutic combination as a combined formulation or by alternation to a mammal, wherein the therapeutic combination comprises a therapeutically effective amount of GDC-0941, and a therapeutically effective amount of one or more an endocrine therapy agents selected from fulvestrant and letrozole. Therapeutic combinations of: (1) GDC-0941 and (2) an endocrine therapy agent may be employed for the treatment of a hyperproliferative disease or disorder, including hematopoietic malignancy, tumors, cancers, and neoplastic tissue, along with pre-malignant and non-neoplastic or non-malignant hyperproliferative disorders. In one embodiment, a human patient is treated with a therapeutic combination and a pharmaceutically acceptable carrier, adjuvant, or vehicle, wherein GDC-0941, or metabolite thereof, of said therapeutic combination is present in an amount to detectably inhibit PI3 kinase activity.

Hematopoietic malignancies include non-Hodgkin's lymphoma, diffuse large hematopoietic lymphoma, follicular lymphoma, mantle cell lymphoma, chronic lymphocytic leukemia, multiple myeloma, AML, and MCL.

Another aspect of this invention provides a pharmaceutical composition or therapeutic combination for use in the treatment of the diseases or conditions described herein in a mammal, for example, a human, suffering from such disease or condition. Also provided is the use of a pharmaceutical composition in the preparation of a medicament for the treatment of the diseases and conditions described herein in a warm-blooded animal, such as a mammal, for example a human, suffering from such disorder.

Articles of Manufacture

In another embodiment of the invention, an article of manufacture, or "kit", containing GDC-0941 useful for the treatment of the diseases and disorders described above is provided. In one embodiment, the kit comprises a container comprising GDC-0941. The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold GDC-0941 or a formulation thereof which is effective for treating the condition and may have a sterile access port (for example, the container may be an intravenous solution bag or a vial having a stopper pierceable by a hypodermic injection needle). At least one active agent in the composition is GDC-0941. The label or package insert indicates that the composition is used for treating the condition of choice, such as cancer. In one embodiment, the label or package inserts indicates that the composition comprising a Formula I compound can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of GDC-0941 and, if present, the second pharmaceutical formulation. For example, if the kit comprises a first composition comprising GDC-0941 and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of GDC-0941, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with GDC-0941 contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Where the kit comprises GDC-0941 and a second therapeutic agent, i.e. the therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

EXAMPLES

Example 1

Clinical Study of Treatment of Luminal A-type Breast Cancer Patients with GDC-0941

Trial Design: A multicenter, international, randomized, double-blinded, placebo-controlled, Phase II trial was conducted for patients with advanced or metastatic breast cancer (MBC) who have previously received treatment with an aromatase inhibitor and experienced recurrence or progression while receiving AI (aromatase inhibitor) therapy. Patients received treatment with (1) GDC-0941 340 mg+fulvestrant, (2) placebo+fulvestrant, or (3) placebo. Patients received intramuscular (IM) fulvestrant 500 mg on Days 1 (prior to randomization) and 15 (following randomization) of Cycle 1 and Day 1 of Cycle 2 and every 28 days thereafter in combination with the following experimental treatments administered orally once daily starting on Day 15 of Cycle 1 and administered continually.

The study was designed to estimate the effect of the addition of GDC-0941 to fulvestrant on PFS compared with single-agent fulvestrant. These comparisons were performed in all treated patients (independent of results from the diagnostic assessments of the tumor) and in specific subsets of diagnostic-positive patients (see the Assay Methods section). Efficacy tumor assessment was performed at screening; at the end of Cycles 2, 4, 6, 8, and 11; and every 12 weeks thereafter prior to the initiation of study treatment on Day 1 of the following cycle. See FIG. 1.

The primary end point was progression-free survival (PFS), on the basis of radiographic studies assessed by the local investigator in all treated patients and patients with PIK3CA-mutant tumors.

Enrollment for this study includes randomized patients who have an activating mutation in the PIK3CA gene and who have a loss of PTEN expression (and PIK3CA wild type) based on the projected prevalence of these diagnostic subsets in patients with ER-positive MBC (Saal et al. (2005) Cancer Res 65:2554-9; Stemke-Hale et al. (2008) Cancer Res 68:6084-91). This sample allows an informative evaluation of the two experimental agents in both the overall population and the biomarker-positive and -negative subsets (see the Statistical Methods section). If the prevalence of patients with biomarker-positive tumors is lower than projected, eligibility may be further restricted to patients whose tumors contain either a PIK3CA mutation or loss of PTEN protein (see the Statistical Methods section) once the sufficient number of patients with wild-type tumors is randomized.

Prospective analysis of PIK3CA mutation status and PTEN expression in archival tumor samples was required prior to randomization. To minimize the possibility of delaying treatment to complete the molecular analysis of archival tumor samples required for patient stratification, a single dose of intramuscular (IM) fulvestrant (500 mg) was given to patients who qualify for enrollment on Cycle 1 Day 1 (which will initiate the fulvestrant "run-in" period), prior to randomization.

Patients were randomized during the fulvestrant run-in period (Cycle 1 Day 1 to Cycle 1 Day 14) to the experimental treatment arms in a 1:1:1 ratio (GDC-0941 340 mg: GDC-0980 30 mg: placebo corresponding to either GDC-0941 340 mg or GDC-0980 30 mg). Patients received fulvestrant 500 mg on Day 15 of Cycle 1 (following randomization) and Day 1 of subsequent 28-day cycles in combination with GDC-0941, GDC-0980 or placebo administered orally once daily starting on Day 15 of Cycle 1.

Three variables were used to stratify patients: PI3K pathway alteration status, resistance to prior AI therapy (primary or secondary resistance), and measurable disease (vs. non-measurable). Primary resistance is defined as either 1) disease relapse during or within 6 months (i.e., 26 weeks) of completing AI treatment in the adjuvant setting, or 2) disease progression within 6 months of starting AI treatment and no response to AI treatment in the metastatic setting. Secondary resistance is defined as SD for a minimum of 6 months, or complete response (CR) or PR to prior metastatic AI treatment. Patients were allocated to the study arms through use of a dynamic hierarchical randomization algorithm with use of predefined stratification variables. Patients received study treatment until progression, intolerable toxicity, elective withdrawal from the study, or study completion or termination. Patients receiving placebo had the opportunity to receive open-label crossover therapy that to receive the experimental study treatment that matches the placebo they received. The protocol provided detailed guidelines for dose interruptions or reductions for the study drug treatments for adverse events.

Outcome Measures: The primary efficacy outcome measure in all treated patients and in patients with PI3K pathway abnormalities is: PFS (progression-free survival), defined as the time from the first dose of fulvestrant on Cycle 1 Day 1 to the first observation of disease progression as assessed by the investigator per modified Response Evaluation Criteria in Solid Tumors Version 1.1 (RECIST v1.1) or death from any cause on study (≤30 days after the last dose of study treatment). The secondary activity outcome measures in all treated patients and in patients with PI3K pathway abnormalities are the following:

Rate of unconfirmed and confirmed objective tumor response as assessed by the investigator per modified RECIST v1.1

Clinical benefit rate as defined by the percentage of patients who experienced a complete response (CR), partial response, or stable disease for at least 24 weeks Duration of confirmed objective response, defined as the time from first observation of an objective tumor response until first observation of disease progression as assessed by the investigator per modified RECIST v1.1, latest tumor assessment of stable disease or better, or death from any cause on study (≤30 days after the last dose of study treatment)

OS is defined as the time from treatment initiation until death from any cause. The safety and tolerability of fulvestrant when combined with GDC-0941, or placebo will be assessed using the following outcome measures:

Incidence, nature, and severity of AEs, graded according to the NCI CTCAE v4.0

Clinically significant changes in vital signs, physical findings, and clinical laboratory results during and following administration of study treatment. The pharmacokinetic (PK) outcome measures are parameters (AUC0-last, Cmax, Cmin) of GDC-0941 single-point concentrations of fulvestrant.

Exploratory outcome measures are the following:

Genomewide measurements in tumor DNA and RNA, including mutational status, RNA gene-expression values, DNA copy number, and protein expression Enumeration of CTCs and PIK3CA mutation status in ctDNA from peripheral blood Patient-reported outcomes of HRQL and symptom severity and interference, to be assessed using the European Organization for Research and Treatment of Cancer (EORTC) QLQ-C30, QLQ-BR23 (Appendix K), mBPI-sf, and a daily pain diary Patients: Eligibility criteria for this study were selected to enhance the safety of patients in this trial. A number of exclusion criteria are specifically based on the known safety profiles of the study drug treatments, as well as nonclinical and clinical data for GDC-0941. Key inclusions criteria were as follows: postmenopausal women age ≥18 years with estrogen receptor-positive, human epidermal growth factor receptor type 2 (HER2)-negative advanced or metastatic breast cancer that, per national or local treatment guidelines, treatment with endocrine therapy (i.e., fulvestrant) is recommended and treatment with cytotoxic chemotherapy is not necessary for patients, at time of entry into the study. In Part I of the study, patients had to have experienced disease relapsed during treatment with (or within 6 months after discontinuation of) an AI in the adjuvant setting or progressed during treatment with an AI in the metastatic setting. The AI must be most recent treatment prior to enrollment and patients must have received at least 4 weeks of treatment with an AI prior to recurrence or disease progression. In Part II of the study, patients had to have experienced disease has progressed during or after treatment with an AI. Patients who discontinued the AI for toxicity rather than completion of regimen or for disease progression are not eligible.

Other key inclusion criteria included Eastern Cooperative Oncology Group (ECOG) Performance Status of 0 or 1, all patients must consent to the providing a tumor sample of their disease, measurable disease by RECIST v1.1 or disease with radiologic scans within 28 days of Day 1 of Cycle 1, adequate hematologic and end-organ function.

Key exclusion criteria included: (1) prior treatment with fulvestrant, PI3K inhibitor, or mTOR inhibitor for advanced breast cancer or MBC, (2) patients requiring anti-hyperglycemic therapy, prior anti-cancer therapy or radiotherapy within 2 weeks prior to Day 1 of Cycle 1, (3) prior treatment with one cytotoxic chemotherapy regimens or (4) experienced recurrent or progressive disease on two endocrine therapies for MBC. Patients requiring anti-hyperglycemic therapy, those with clinically significant cardiac, pulmonary dysfunction, active autoimmune disease, immunocompromised status, clinically significant history of liver disease, and those with untreated or active central nervous system (CNS) metastases were also excluded from study participation. Written informed consent was obtained from all patients before enrollment.

Assay Methods: Mutational analysis for PI3K: Somatic mutations in the PIK3CA gene are found in approximately 30% of breast cancers and occur most commonly in Exons 9 and 20 in the codons encoding amino acids E542, E545, and H1047. Real-time PCR (RT-PCR) assays that amplify Exons 9 and 20 of PIK3CA offer a sensitive and quantitative method to detect mutations from archival tumor material. DNA will be extracted from tumor samples and subjected to quantitative RT-PCR (qRT-PCR) assays that detect the wild-type allele, as well as assays for nucleotide substitutions that include but are not limited to the following amino acid changes: E542 (K), E545 (A, G, or K), and H1047 (L, R, Y). Assays from all samples will be run on Cobas z 480 Analyzer® (Roche Molecular Diagnostics) for quantitative real-time PCR, and mutation calls will be made using appropriate cut-offs and automated software. Following histopathological review, samples with <20% tumor content will be enriched for tumor content by macro- or microdissection.

For patient stratification purposes, a PIK3CA mutant-containing tumor is defined as a sample that contains any one of the predefined, activating mutations. A PIK3CA wild-type designation is defined as a sample that does not contain any of the predefined, activating mutations. A designation of PIK3CA status unknown is a sample wherein any one of the predefined mutations was not definitively assessed AND in the absence of any additional activating mutations. In addition, ctDNA will be extracted from plasma samples collected from patients and will be used for the detection of oncogenic mutations through use the qRT-PCR assays described above. The prevalence of the mutations measured at baseline and after treatment may provide information on response or resistance to therapy. Results from the analysis of ctDNA will not be used to stratify patients for randomization purposes.

PTEN status is examined by IHC through use of a protocol that has been validated for specificity with use of several available cell line controls. Archival tumor material will be scored only if appropriate staining is observed in internal control stromal or normal (non-tumor) tissue elements. PTEN status may also be examined by qRT-PCR assay for mRNA levels or chromosomal loss in a fluorescence in situ hybridization (FISH) assay.

ER (estrogen receptor) and PgR (progesterone receptor) status will be confirmed using IHC assays run under appropriate College of American Pathologists (CAP)/American Society of Clinical Oncology guidelines in a CAP-accredited laboratory, in order to confirm the diagnosis of HR-positive breast cancer. The rePatisults of this analysis will not be required to satisfy enrollment criteria and may not be available prior to patient randomization. If the results from the central laboratory analysis suggest that a patient's tumor is ER– and PgR-negative, the treating investigator will be informed of this result, and the patient's continued participation in the study will be at the discretion of the treating investigator.

HER2 status: Tumor samples will also be tested for HER2 protein overexpression by IHC through use of the DAKO HercepTest kit according to the instructions in the HercepTest Package Insert. An IHC result of 3+ will be considered HER2 positive. An IHC result of 2+ will be considered ambiguous, and tissue will be tested for HER2 gene amplification. HER2 gene amplification will be assessed on archival primary tumor material through use of the standard PathVysion® HER2 FISH kit (Abbott Laboratories) according to the instructions in the PathVysion Package Insert.

DNA obtained from FFPE sections may also be analyzed for mutations or copy number alterations in relevant oncogenes and tumor suppressor genes. Specifically, a multiplex mutation assay based on the TAQMAN® (Life Technologies) platform will be used to determine mutation status in KRAS, NRAS, BRAF, EGFR, and AKT1. These assays may also be performed on ctDNA if sufficient sample remains after running the PIK3CA mutation assay. qPCR-based copy number assays for c-MYC, CCND1, FGFR1, FGFR2, IGF1R, PIK3CA, CDK4, and potentially other genes involved in PI3K signaling will be performed on the ABI7900® (Life Technologies) platform.

If sufficient DNA remains after the assays above have been performed, genomewide methods for mutation detection may be performed. The goal of exon resequencing is twofold. One goal is to interrogate a host of known genes of potential interest for endocrine resistance or response/resistance to the study treatments. Examples include other genes in the PI3K pathway, other RTKs, known tumor-suppressor genes, and others for which there is a logical preexisting hypothesis that could be related to endocrine biologic resistance or study treatment response. A second goal is to perform a broader hypothesis-generating analysis to assess whether any protein-coding mutations in the genome occur at greater or less frequency in patients whose tumors have become resistant to endocrine therapy or that correlate with response/resistance to the study treatments. There are two methods currently being explored and evaluated for exon resequencing: scanning for known mutations with use of the sensitive mass spectrometry-based Sequenom system and the evolving technology of exon capture resequencing (Hodges et al. (2007) Nat Genet 39:1522-7). One or both methods may be used. Given that the field of genomewide sequencing is rapidly evolving, it is also possible that another technology will be implemented, depending on the field and the level of validation at the time that biopsies from this trial are to be analyzed. In cases where the tumor tissue does not produce sufficient DNA for exon resequencing, whole-genome amplification will be used. If available, remaining DNA isolated from frozen, non-FFPE tissue may be utilized for DNA copy number profiling. Whole genome-amplified material will be used where necessary. A commercially available array Comparative Genomic Hybridization platform (Agilent Co.) will be used. The goal will be to develop a database of copy number changes that can be interrogated to ask hypothesis-driven questions or to identify novel predictors of response.

In cases where there is sufficient archival or fresh tissue to isolate RNA, gene mRNA and MiRNA expression profiling analysis of a panel of genes important in breast cancer, PI3K signaling, and/or endocrine-therapy resistance will be performed. In the event that frozen tumor tissue is available, RNA will be extracted and profiled for global gene expression or miRNA levels through use of a validated commercially available platform such as Affymetrix or Agilent. The goal will be to examine whether there are gene-expression patterns that are associated with clinical response Immunohistochemistry Assays: Ki67 antigen is an important cell cycle-related nuclear protein that is expressed by proliferating cells in all phases of the active cell cycle (G1, S, G2, and M phase). As such, it is a useful marker of the proliferative state of a tumor. Ki67 protein levels will be determined by IHC through use of standard techniques. If sufficient sections remain, IHC may also be performed for analytes such as pPRAS40, p4EB-P1, and pS6, because phosphorylation of these proteins may correlate with the pathway activation status in neoplastic cells.

Reverse-Phase Protein Arrays: Reverse-phase protein arrays offer the potential to profile hundreds of possible phosphorylation events in very small quantities of tumor material such as might be obtained from laser-capture microdissection from a biopsy or from archival frozen, non-FFPE tissue. The basis of the technology is to immobilize small amounts of lysate from a cell line or tumor sample in serial dilution on a microarray slide. Multiple samples are thus arrayed on a slide and can be probed with antibodies that detect a particular phospho-epitope. Using this technology, we will profile 100 key signaling nodes representing a number of pathways known to be dysregulated in breast cancer, including but not limited to receptors in the HER family and multiple components of PI3K/mTOR-, estrogen-, and RAS/MAPK-signaling pathways.

Circulating Tumor Cell Analysis: CTC analysis will be performed on whole blood through use of the Cellsearch, Biocept, Cellective, and/or other CTC enumeration and molecular profiling platforms. CTCs isolated from blood will undergo molecular analysis such as PI3K mutation status and PTEN status. Results from the CTC analysis will not be used to stratify patients for randomization purposes.

Pharmacokinetic Assays: Plasma samples will be evaluated for GDC-0941, and fulvestrant through use of a validated liquid chromatography tandem mass spectrometry (LC-MS/MS) assay. Samples may be used for exploratory evaluation of GDC-0941-related metabolites, additional pharmacodynamic development, and/or determination of fulvestrant plasma levels.

DNA for Exploratory Pharmacokinetic/Pharmacodynamic Genotype-Phenotype Relationships: It is established that genetic variants of drug-metabolizing enzymes and transporters can affect the PK of drugs, which affects their safety and efficacy. For example, patients who carry defective alleles of the gene encoding uridine diphosphate glucuronosyltransferase 1A1, which facilitates the metabolism and excretion of SN-38 (the active metabolite of irinotecan), are at higher risk for adverse effects associated with the use of standard doses of irinotecan (O'Dwyer and Catalano (2006) J Clin Oncol 24:4534-8). Preliminary results from in vitro metabolism studies with GDC-0941 suggest that they are partially metabolized by multiple Phase I cytochrome P450 enzymes, including CYP2C8 and CYP3A4/5. Although in vitro studies can help elucidate the roles of enzymes in the metabolism of the drug, these results are not always predictive of in vivo metabolism for a number of reasons, such as differences in drug concentrations that the enzymes encounter in vitro and in vivo. For this reason, a blood sample for DNA isolation will be collected from all patients in this study for potential pharmacogenetic analysis of genes or biomarkers that may affect the PK of GDC-0941. The decision to analyze the samples will be based on a review of the PK data. The genotyping efforts will also be guided using results from the in vitro metabolism and the totality of clinical pharmacology data available for each molecule. The analysis will be performed on identifiable DNA samples, because it is necessary to link a patient's PK data with genotype. This analysis would be restricted to the evaluation of genes that may be involved in the PK GDC-0941 (e.g., drug metabolism, disposition, or elimination) and/or pharmacodynamic response. Samples may be stored and analyzed up to 2 years after the completion of the study, at which time all DNA samples collected for this analysis will be destroyed.

Statistical Methods: There will be no adjustments made for multiple comparisons when addressing primary and secondary endpoints. Multiple comparisons adjustments will be used in the individual exploratory endpoints to account for genomewide correlative comparisons. With the assumption of an overall enrollment rate of 0.14 patients per month per site, it is expected that the preplanned safety analyses of the Safety Cohort, after 30 and 90 patients have completed 8 weeks and after 90 events of progressive disease have occurred, will take place at approximately 9 and 17 months, respectively, after the first patient is enrolled. It is expected that the final analysis will take place at approximately 27 months after the first patient is enrolled.

Efficacy Analysis: The primary efficacy analyses will be performed on all randomized patients who are confirmed to be ER positive and/or PgR positive on the basis of the results performed on at the central laboratory. If there is a substantial number of patients whose tumor is ER and PgR negative based on the analysis performed at the central laboratory, then additional patients may be enrolled to satisfy the enrollment requirements needed to support the primary objectives of the study. Additional sensitivity analyses may include all patients who were randomized and received at least one dose of any of the study drugs. The primary efficacy analyses will be triggered by occurrence of the prespecified number of total events in the two diagnostic subgroups (45 events in PTEN-null patients and 60 events in PI3KCA-mutant patients). PFS and duration of the confirmed response will be evaluated using unstratified survival analysis. Additional stratified sensitivity analyses will also be performed. Kaplan-Meier curves will be produced for all patients in primary efficacy analyses and in sensitivity analyses and, similarly, for patients in each of the diagnostic PI3K pathway strata (i.e., PIK3CA mutant, PTEN null, dual wild type, PI3KCA-mutant/PTEN-null combined, and "unknown"). The unstratified hazard ratio estimate of PFS comparing fulvestrant in combination with either GDC-0941 versus fulvestrant+placebo and the 90% confidence interval (CI) will be provided overall and by the PI3K pathway alteration strata. Additional analyses will include hazard ratio estimates of the PFS through use of stratified log-rank test.

Data for randomized patients without disease progression or death will be censored at the date of the last tumor assessment (or, if no tumor assessments were performed after the baseline visit, at the date of the first fulvestrant treatment on Day 1 of Cycle 1 plus 1 day). Data for patients who are lost to follow-up will be censored at the last date of tumor assessment at which the patient was known to be progression free. An estimate of the best (confirmed and unconfirmed) tumor response together with 90% CI will be evaluated for each treatment arm through use of categorical analyses. The difference in tumor response rates in the fulvestrant+GDC-0941 versus fulvestrant+placebo arms will be calculated, and the 90% CI will be provided overall and by the PI3K strata. The same method will be used to analyze the disease stabilization and CBR. Duration of the confirmed response and OS will be analyzed using the same method as for the PFS endpoint. Efficacy data for the cross-over patients after their cross-over will be summarized separately by study arm through use of the first day of their receiving a cross-over treatment as the baseline for the evaluation of the PFS and their last scan prior to cross-over treatment initiation as baseline tumor measurement.

Selected sections from the Response Evaluation Criteria in Solid Tumors (RECIST), Version 1.1, (Eisenhauer E A, Therasse P, Bogaerts J, et al. New response evaluation criteria in solid tumors: revised RECIST guideline (version 1.1). Eur J Cancer (2009) 45:228-47) are presented below, with slight modifications and the addition of explanatory text as needed for clarity.

Measurability of Tumor at Baseline: At baseline, tumor lesions/lymph nodes will be categorized as measurable or nonmeasurable as described below.

Tumor Lesions: Tumor lesions must be accurately measured in at least one dimension (longest diameter in the plane of measurement is to be recorded) with a minimum size as follows:
- 10 mm by computed tomography (CT) or magnetic resonance imaging (MRI) scan (CT/MRI scan slice thickness/interval no greater than 5 mm)
- 10-mm caliper measurement by clinical examination (lesions that cannot be accurately measured with calipers should be recorded as nonmeasurable)
- 20 mm by chest X-ray Malignant Lymph Nodes. To be considered pathologically enlarged and measurable, a lymph node must be ≥15 mm in the short axis when assessed by CT scan (CT scan slice thickness recommended to be no greater than 5 mm).

At baseline and follow-up, only the short axis will be measured and followed. See also notes below on "Baseline Documentation of Target and Non-Target Lesions" for information on lymph node measurement.

Response Criteria

Evaluation of Target Lesions: The criteria used to determine objective tumor response for target lesions are:
- Complete response (CR): Disappearance of all target lesions, Any pathological lymph nodes (whether target or non-target) must have reduction in short axis to <10 mm.
- Partial response (PR): At least a 30% decrease in the sum of diameters of target lesions, taking as reference the baseline sum of diameters
- Progressive disease (PD): At least a 20% increase in the sum of diameters of target lesions, taking as reference the smallest sum on study (nadir), including baseline. In addition to the relative increase of 20%, the sum must also demonstrate an absolute increase of at least 5 mm.

The appearance of one or more new lesions is also considered progression.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

We claim:

1. A method of treatment comprising administering a therapeutically effective amount of GDC-0941 and an endocrine therapy agent to a patient with PR+or luminal A-type breast cancer, wherein GDC-0941 has the structure:

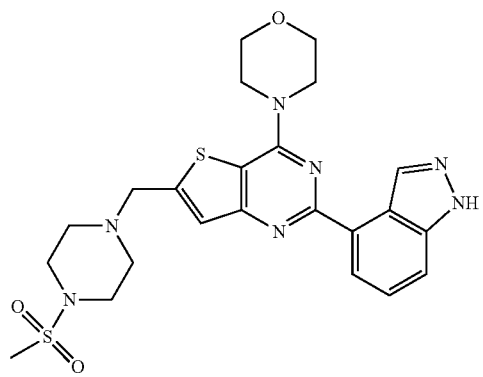 [SMILES: CS(=O)(=O)N1CCN(Cc2cc3nc(-c4cccc5[nH]ncc45)nc(N4CCOCC4)c3s2)CC1]

including stereoisomers, geometric isomers, tautomers, or pharmaceutically acceptable salts thereof;
wherein GDC-0941 is administered daily at three week or four week intervals to the patient, or is administered daily for five days followed by a two-day holiday;
and wherein the endocrine therapy agent is selected from the group consisting of fulvestrant, letrozole, tamoxifen, and exemestane.

2. The method of claim 1 wherein GDC-0941 is the bis methanesulfonate salt.

3. The method of claim 1 wherein the patient has been previously treated with chemotherapy, radiotherapy, and/or surgical resection.

4. The method of claim 1 wherein the patient has been previously treated with an endocrine therapy agent.

5. The method of claim 1 wherein the patient has been previously treated with an aromatase inhibitor.

6. The method of claim 5 wherein the aromatase inhibitor is selected from the group consisting of letrozole, anastrozole and exemestane.

7. The method of claim 4 wherein the patient has relapsed.

8. The method of claim 1 wherein the PR+ or luminal A-type breast cancer is metastatic.

9. The method of claim 3, wherein the patient has been previously treated with one or more therapeutic agents selected from the group consisting of tamoxifen, fulvestrant, everolimus, exemestane, and letrozole.

10. The method of claim 1 wherein GDC-0941 is administered daily at three week or four week intervals to the patient.

11. The method of claim 10 wherein the three week or four week interval is followed by a one week holiday interval where the patient is not administered GDC-0941.

12. The method of claim 1 wherein GDC-0941 is administered daily for five days followed by a two day holiday.

13. The method of claim 1 wherein GDC-0941 is administered orally.

14. The method of claim 1 wherein the therapeutically effective amount of GDC-0941 is between 200 and 400 mg per day.

15. The method of claim 1 wherein the endocrine therapy agent is fulvestrant.

16. The method of claim 1 wherein the endocrine therapy agent is letrozole and the therapeutically effective amount of letrozole is 1 to 10 mg per day.

17. The method of claim 1 wherein the patient is administered the endocrine therapy agent and subsequently administered GDC-0941.

18. The method of claim 1 wherein administration of GDC-0941 and the endocrine therapy agent results in a synergistic effect.

19. The method of claim 1 wherein the PR+, luminal A-type breast cancer expresses a PIK3CA mutant selected from E542K, E545K, H1047L and H1047R.

20. The method of claim 1 wherein the PR+, luminal A-type breast cancer expresses a PTEN mutant.

21. The method of claim 1 wherein the patient is HER2 negative, and ER (estrogen receptor) positive.

22. The method of claim 1 wherein a biological sample obtained from the patient, prior to administration of the combination to the patient, has been tested for PIK3CA or PTEN mutation status, and wherein PIK3CA or PTEN mutation status is indicative of therapeutic responsiveness by the patient to GDC-0941.

23. The method of claim 1 wherein a biological sample obtained from the patient is tested by measuring functional PI3K protein level after administration of GDC-0941, wherein a change in the level of functional PI3K protein indicates that the patient will be resistant or responsive to GDC-0941.

24. A method of selecting patients with PR+, luminal A-type breast cancer for treatment with GDC-0941 comprising:
(a) detecting a PIK3CA or PTEN mutation in a biological sample obtained from the patient; and
(b) comparing PIK3CA or PTEN mutation status in a biological sample obtained from the patient prior to administration of GDC-0941 or a combination of GDC-0941 and a therapeutic agent to the patient,
wherein a change or modulation of PIK3CA or PTEN mutation status in the sample obtained following administration of GDC-0941 or the combination of GDC-0941 and a therapeutic agent identifies a patient who will respond to treatment with GDC-0941; and
wherein the therapeutic agent is selected from the group consisting of fulvestrant, letrozole, tamoxifen, and exemestane.

25. A method of monitoring therapeutic efficacy in patients with PR+, luminal A-type breast cancer comprising:
(a) treating the patient with GDC-0941 or a combination of GDC-0941 and a therapeutic agent;
(b) measuring functional PI3K protein level in a biological sample obtained from the patient after administration of GDC-0941 or the combination of GDC-0941 and a therapeutic agent; and
(c) altering the dosage of GDC-0941, the frequency of dosing GDC-0941, or the course of therapy administered to the patient; and
wherein the therapeutic agent is selected from the group consisting of fulvestrant, letrozole, tamoxifen, and exemestane.

26. A method of optimizing therapeutic efficacy of GDC-0941 or a combination of GDC-0941 and a therapeutic agent in the treatment of PR+, luminal A-type breast cancer, the method comprising:
(a) detecting a PIK3CA or PTEN mutation in a biological sample obtained from a patient following administration of at least one dose of GDC-0941 or the combination of GDC-0941 and a therapeutic agent; and
(b) comparing the PIK3CA or PTEN status in a biological sample obtained from the patient prior to administration of GDC-0941 or the combination of GDC-0941 and a therapeutic agent to the patient,
wherein a change or modulation of PIK3CA or PTEN in the sample obtained following administration of GDC-0941 or the combination of GDC-0941 and a therapeutic agent identifies a patient who has an increased likelihood of benefit from treatment with GDC-0941 or the combination of GDC-0941 and a therapeutic agent; and
wherein the therapeutic agent is selected from the group consisting of fulvestrant, letrozole, tamoxifen, and exemestane.

27. A method of identifying a biomarker for monitoring responsiveness to GDC-0941 or a combination of GDC-0941 and a therapeutic agent in the treatment of PR+, luminal A-type breast cancer, the method comprising:
(a) detecting the expression, modulation, or activity of a biomarker selected from a PIK3CA or PTEN mutation in a biological sample obtained from a patient who has received at least one dose of GDC-0941 or the combination of GDC-0941 and a therapeutic agent; and
(b) comparing the expression, modulation, or activity of the biomarker to the status of the biomarker in a reference sample wherein the reference sample is a biological sample obtained from the patient prior to administration of GDC-0941 or the combination of GDC-0941 and a therapeutic agent to the patient;

wherein the modulation of the biomarker changes by at least 2 fold lower or higher compared to the reference sample is identified as a biomarker useful for monitoring responsiveness to GDC-0941 or the combination of GDC-0941 and a therapeutic agent; and wherein the therapeutic agent is selected from the group consisting of fulvestrant, letrozole, tamoxifen, and exemestane.

* * * * *